(12) United States Patent
Strizhkov et al.

(10) Patent No.: US 6,642,000 B1
(45) Date of Patent: Nov. 4, 2003

(54) PCR AMPLIFICATION ON MICROARRAYS OF GEL IMMOBILIZED OLIGONUCLEOTIDES

(75) Inventors: Boris Strizhkov, Moscow Region (RU); Sergei Tillib, Hinsdale, IL (US); Vladimir Mikhailovich, Woodridge, IL (US); Andrei Mirzabekov, Darien, IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 09/559,306

(22) Filed: Apr. 25, 2000

Related U.S. Application Data

(60) Provisional application No. 60/165,029, filed on Nov. 12, 1999.

(51) Int. Cl.[7] .............................. C12Q 1/68; C12P 19/34
(52) U.S. Cl. ............................. 435/6; 435/91.2
(58) Field of Search .................... 435/6, 91.1, 91.2; 536/22.1, 23.1

(56) References Cited

U.S. PATENT DOCUMENTS

| | | | |
|---|---|---|---|
| 5,518,900 A | | 5/1996 | Nikiforov et al. |
| 5,578,458 A | | 11/1996 | Caskey et al. |
| 5,846,710 A | | 12/1998 | Bajaj |
| 5,851,772 A | * | 12/1998 | Mirzabekov et al. ......... 435/6 |
| 5,888,819 A | | 3/1999 | Goelet et al. |
| 6,004,744 A | | 12/1999 | Goelet et al. |
| 6,013,432 A | | 1/2000 | Luciw et al. |

OTHER PUBLICATIONS

Waters LC, Jacobson SC, Kroutchinia N, Khandurina J, Foote RS and Ramsey JM. Multiple sample PCR amplification and electrophoretic analysis on a microchip. Anal-.chem. 70, 5172–5176, 1998.*

Arenkov P., et al. (2000) "Protein Microchips: Use for Immunoassay and Enzymatic Reactions" *Anal Biochem* 278, 123–131.

Dubiley, S., et al. (1997) "Fractionation, Phosphorylayion, and Ligation on Oligonucleotide Microchips to Enhanced Sequencing by Hybridization" *Nucl Acids Res* 25,2259–2265.

Dubiley, S., et al. (1999) "Polymorphism Analysis and Gene Detection by Minisequencing on an Array of Gel–Immobilized Primers" *Nucl Acids Res* 27, e19.

Fotin, A., et al. (1998) "Parallel Thermodynamic Analysis of Duplexes on Oligodeoxyribonucleotide Microchips" *Nucl Acids Res* 26, 1515–1521.

Proudnikov, D., et al. (1998) "Immobilization of DNA in Polyacrylamide Gel for the Manufacture of DNA and DNA–Oligonucleotide Microchips" *Andy Biochem* 259, 34–41.

Yershov, G., et al. (1996) "DNA Analysis and Diagnostics on Olignucleotide Microchips" *Proc Natl Acad Sci USA* 93,4913–4918.

* cited by examiner

*Primary Examiner*—Eggerton A. Campbell
*Assistant Examiner*—Suryaprabha Chunduru
(74) *Attorney, Agent, or Firm*—Alice O. Martin; Barnes & Thornburg

(57) ABSTRACT

The invention relates two general methods for performing PCR amplification, combined with the detection and analysis of the PCR products on a microchip. In the first method, the amplification occurs both outside and within a plurality of gel pads on a microchip, with at least one oligonucleotide primer immobilized in a gel pad. In the second method, PCR amplification also takes place within gel pads on a microchip, but the pads are surrounded by a hydrophobic liquid such as that which separates the individual gel pads into environments which resemble micro-miniaturized test tubes.

28 Claims, 22 Drawing Sheets

A

B

1

2

3

4

A

RNase target
(-riboU-riboU-)

B

A

B

PCR AMPLIFICATION ON MICROARRAYS OF GEL IMMOBILIZED OLIGONUCLEOTIDES

This application claims priority from co-pending provisional application U.S. Ser. No. 60/165,029 filed Nov. 12, 1999.

This invention was conceived under Contract No. W-31-1-0-ENG-39 between the U.S. Department of Energy (DOE) and The University of Chicago representing Argonne National Laboratory. The work was supported by the U.S. Defense Advance Research Project Agency under Interagency Agreement No. AO-E428 by, Grant No. 5/2000 from the Russian Human Genome Program, and by Grant No. a262 from the Moscow Government.

This invention relates to polymerase chain reaction (PCR) amplification using microarrays of gel immobilized oligonucleotide primers in gel pads on a microchip (also known as a biochip). The invention also relates to a method of separating the individual gel pads on a microchip by immersing pads in a hydrophobic liquid, such as oil, as well as to novel structures for the gel pads which improves the efficacy of the PCR reactions in the immersed microchip. The primers can be selectively activated, inactivated, or detached from the gel matrix, and can be selected to perform combinatorial or multiplex PCR amplification.

BACKGROUND OF THE INVENTION

DNA analysis using PCR amplification and detection of target regions of microorganisms is becoming increasingly popular for medical, environmental and military applications. For example, as the threat of international and domestic bioterrorism has heightened over the past few years, *B. anthracis* has arisen as a dangerous bioterrorist agent to be detected. Shiga and Shiga-like toxin genes of the toxin-producing strains of *Shigella dysentariae* and *Escherichia coli*, respectively, inhabiting human intestines are responsible for hemorrhagic colitis and other diseases. Diagnostic assays for these microorganism are useful. International and domestic epidemics of *M. tuberculosis* now include drug resistant strains, are growing in frequency, and now represent a serious public health problem facing the world. Rifampicin is one of the most efficient drugs used to treat tuberculosis patients, so detection is imperative, but mutations occurring within a short region of the rpoB gene account for rifampicin resistance in 96% of *M. tuberculosis* strains. Therefore, it is important to detect these mutations so appropriate treatment is used. Detection of a gene coding for β-lactamase, which inactivates ampicillin, is a good model for screening for bacterial plasmid-born antibiotic resistance.

Polymerase Chain Reaction (PCR) amplification of specific DNA sequences is a powerful analytical tool that has many different applications, but which also has significant limitations. These limitations derive from the repetitious manual sample handling and analysis needed for many applications, i.e., the need for individual sample tubes and gel electrophoresis of the amplified end-products for analysis. At present, there is a rapidly growing need for parallel amplification and analysis of many different samples. Complex, sequential analysis is laborious.

PCR amplification is based on specific hybridization of oligonucleotide primers (relatively short pieces of DNA) that hybridize with longer DNA sequences of interest (target DNA). Currently PCR is usually performed in parallel experiments in different test tubes. Multiplex amplification, in which different amplification primers mixed with DNA molecules or DNA sample pools are carried through the PCR process, has a limit of less than ten different reactions in a single test tube. Therefore, a need exists to develop a simple and efficient method to amplify multiple DNA sequences with multiple primers, in a manner that allows the identification of specific amplified DNA fragments.

A desirable procedure would also be combining DNA amplification with detection and identification of specific sequences by hybridization. An easily used, cost effective method is also desirable.

SUMMARY OF THE INVENTION

The invention relates several general methods for performing PCR amplification combined with the detection and analysis of the PCR products on a microchip.

In one embodiment, PCR amplification takes place within gel pads on a microchip, but the pads are surrounded by a hydrophobic liquid which separates the individual gel pads into environments which resemble micro-miniaturized test tubes. This method comprises the steps of: (a) providing a microchip with immobilized primers; (b) adding a hybridization solution containing a nucleic acid sequence to be tested to the microchip; (c) hybridizing the nucleic acid sequence to the primers; (d) replacing the hybridization solution with an amplification solution, which may also contain an enzyme or reagent which detaches/activates/inactivates a set of primers as discussed below; (e) removing the amplification solution and replacing it with a hydrophobic liquid, such as a hydrocarbon like mineral oil; (f) cycling the PCR at temperatures selected to be effective with one or more sets of PCR primers; and (g) repeating steps (a) to (f) for the different types of primers, thus performing a combinatorial PCR amplification on a microchip. One can use these methods of combinatorial amplification to design "nested" primer experiments, to isolate and amplify sequences with increasing specificity with each repetition.

In another embodiment, the amplification occurs both outside in the solution surrounding the gel pads, and within a plurality of gel pads themselves on a microchip, with at least one oligonucleotide primer immobilized in a gel pad. The method includes the steps of:

(a) providing a microchip with at least one oligonucleotide primer immobilized in gel pads;

(b) adding a solution to the microchip environment comprising an amplification buffer, primers and a nucleic acid sequence to be tested;

(c) cycling the temperature to achieve amplification; and (d) repeating steps (a) to (c) while selectively activating, inactivating or detaching sets of primers within the gel pads.

The individual gel pads enclose a space capable of retaining the solution after the solution is removed from the microchip. At least one of the primers is immobilized in the gel pad. These immobilized primers can also be detachable primers, activatable primers, or inactivatable primers, selected depending on the needs of the experimenter.

For all embodiments there may be an additional step of running a primer extension or ligase reaction, or other related methods to detect and analyze the PCR products of the nucleic acid sequence to be tested.

Types of Primers

The composition of PCR primers suitable for practice of the invention are of two general types: 1) primers that are immobilized onto gel pads on a microchip and are active as PCR primers immediately after immobilization, and 2)

primers that are modulated, which means that their activity as PCR primers can be changed by a separate treatment after immobilization.

There are at least three subtypes of modulated primers. Releasable or detachable (temporary immobilized) primers, are oligonucleotides that contain an oligoribonucleotide (RNA) linker incorporated into the 5'-terminal position of an oligodeoxynucleotide (DNA) primer that is immobilized onto the microchip gel pads, and that can subsequently be detached from the gel-pads by treatment with a ribonuclease. Upon treatment with a specific ribonuclease enzyme, the primer splits at the ribonucleotide residues and is released from the gel matrix within interior of the gel pad. Inactivatable (temporarily active) oligonucleotide primers, are immobilized oligonucleotides that can be inactivated. These primers contain, for example, an oligoribonucleotide chain in the middle or close to the 3' terminal position, of an oligodeoxynucleotide primer. Upon treatment with a ribonuclease, these inactivatable primers can be inactivated.

Finally, activatable (temporarily inactive) oligonucleotide primers are immobilized primers that need to be activated in order to serve as primers. One example of an activatable primer has a phosphorylated 3'-terminal phosphate that prevents the primers from themselves being extended. To activate the primer, the phosphate group is removed by treatment with aphosphatase enzyme, thereby "activating" the primer. One suitable phosphatase enzyme is alkaline phosphatase.

The methods of the invention were applied for detection and mutation analysis of genes from a number of microorganisms of practical importance: anthrax toxin and shiga toxin genes, a plasmid-borne ampicillin resistance gene, and rifampicin-resistant genomic mutations of *M. tuberculosis*.

On-chip amplification was applied to detect 1) anthrax toxin genes; and 2) a plasmid borne β-lactamase gene responsible for bacterial ampicillin resistance. Allele specific on-chip amplification was used to identify a shiga toxin gene and discriminate it from a shiga-like toxin gene. Rifampicin resistant genomic mutations of *Mycobacterium tuberculosis* were detected by on-chip allele specific amplification of the rpoB region of DNA isolated from a human sputum. Gel pads with specific sets of mobilized primers may be separated from each other using mineral oil. Both amplification and hybridization are performed.

Definitions and Abbreviations

Gel matrix=composition such as polyacrylamide gel; gel pad=gel matrix units that form a microchip; ssDNA=single-stranded DNA; dsDNA=double-stranded DNA; F=forward primer; R=reverse primer; I=internal primers; *-P= hybridization oligonucleotide probe; PCR=polymerase chain reaction; and RNase=ribonuclease A.

(b) detection and analysis of PCR product (hybridization with extended region of P2 primer).

(c) detection of the primer P$^r$1 release during the experiment (hybridization with primer P1).

Figure 15:
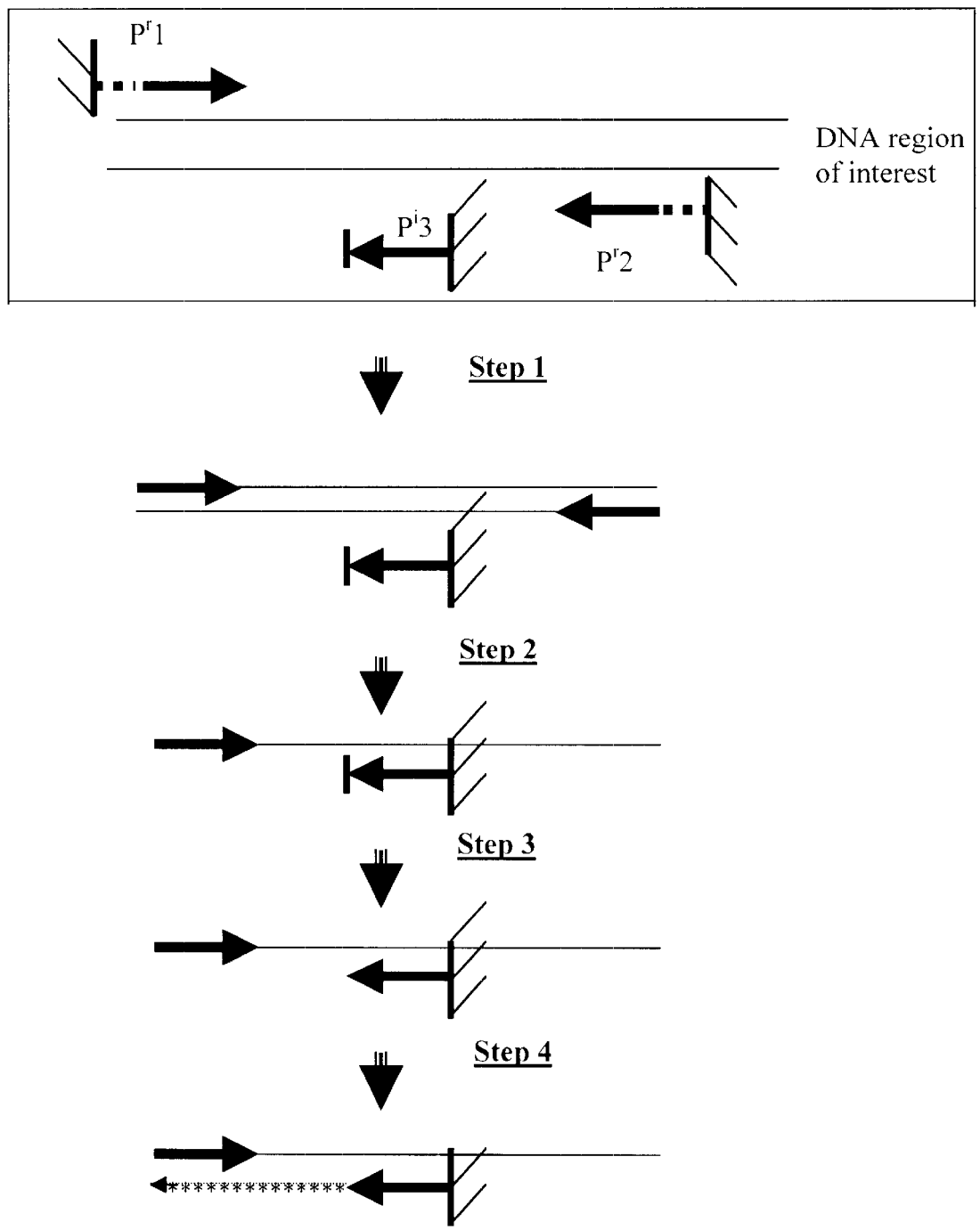

FIG. 15 illustrates combinatorial PCR amplification within a gel pad using three immobilized primers, P$^r$1, P$^r$2 and P$^i$3;

Step 1: The release of P$^r$1 and P$^r$2 primers and the performing of the first PCR step;

Step 2: Hybridization of PCR product to immobilized inactive primer P$^i$3;

Step 3: Activation of the immobilized primer P$^i$3; and

Step 4: An analysis of the amplified sequence using activated primer P3 for primer extension or single base extension reactions.

Figure 16:
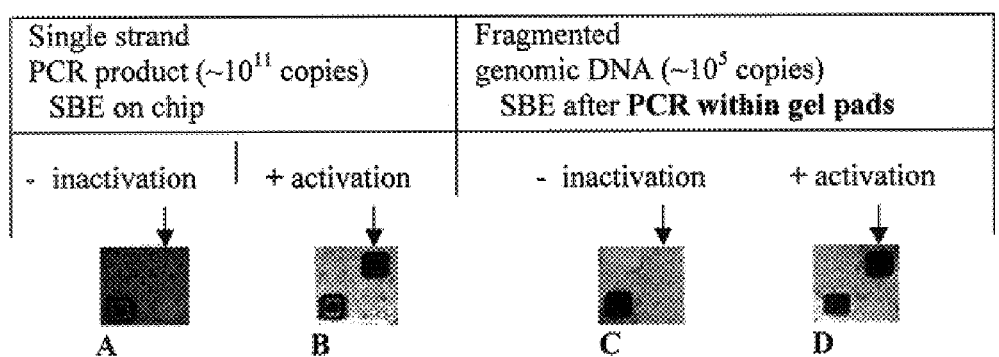

FIG. 16 demonstrates activation of modulated (temporary inactive) immobilized primer P$^i$3.

Figure 17:
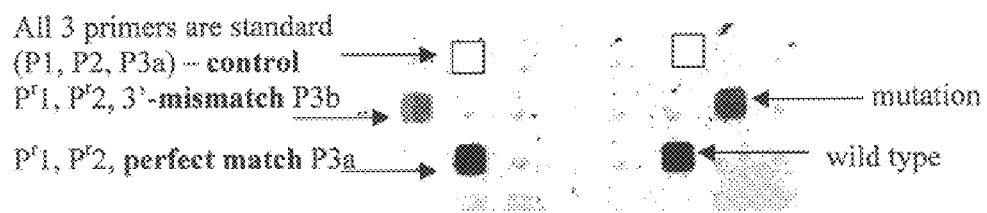

FIG. 17 shows results of combinatorial PCR/mutation detection analysis within gel pads using three immobilized primers, P$^r$1, P$^r$2 (P3b is a mismatch; P3a is a perfect match).

Figure 18:
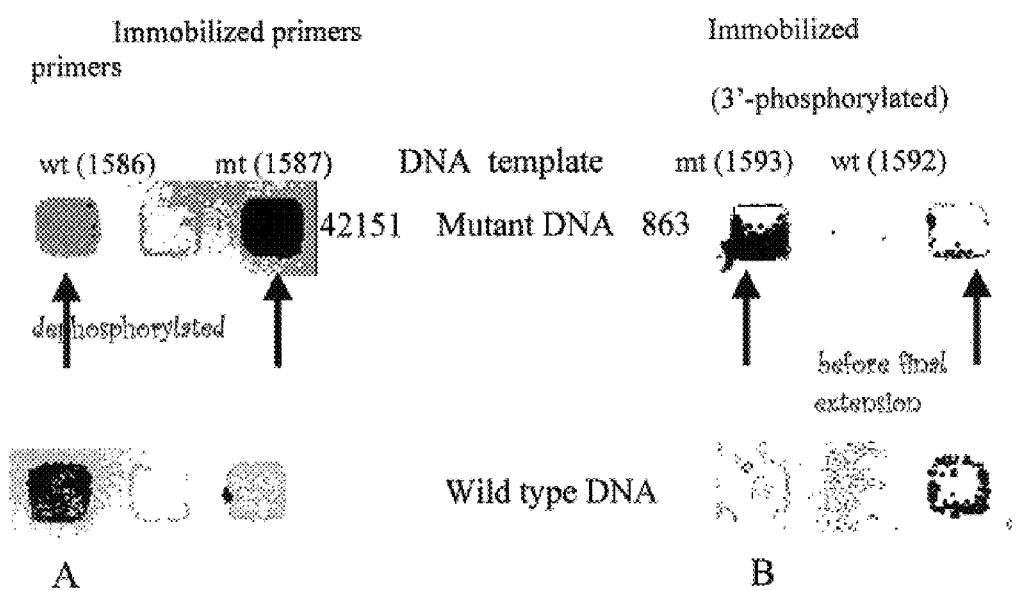

FIG. 18 shows results of combinatorial PCR on a microchip under oil used for mutation detection (as in FIG. 15); a set of three immobilized primers was used; activation of the immobilized P3 primer was done before the final detection step (A) by decreasing the annealing temperature of the PCR reaction; and (B)=by removal of the 3' blocking phosphate group of the temporarily active P3 primer.

Figure 19:
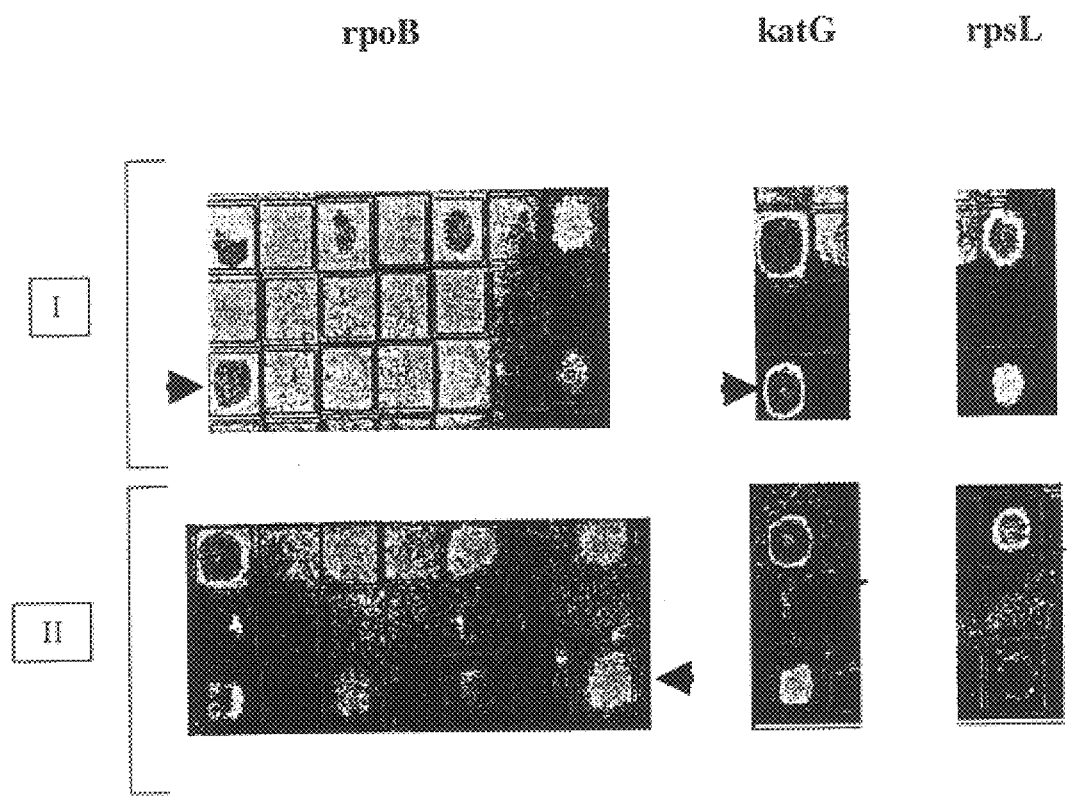

FIG. 19 presents a reproduction of microchips after PCR under oil was performed for synchronous analysis of three genetic regions using independently working gel pads of the same microchip; I=DNA sample with mutations in rpoB and katG; II=DNA sample with mutation in rpob; in both samples there is no mutation in the studied rpsL gene region.

Figure 20:
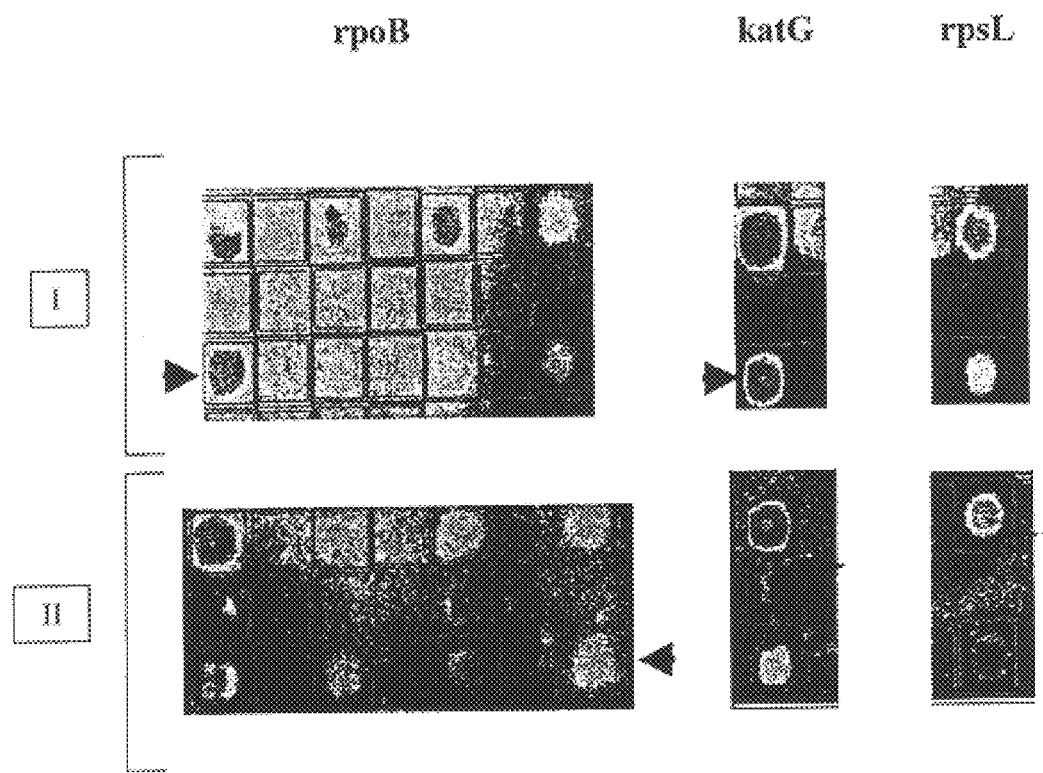

FIG. 20 A shows extended fluorescently labeled, non-phosphorylated primers; B shows incorporation of a fluorescently labeled base into the immobilized primer activated by dephosphorylation.

Figure 21:
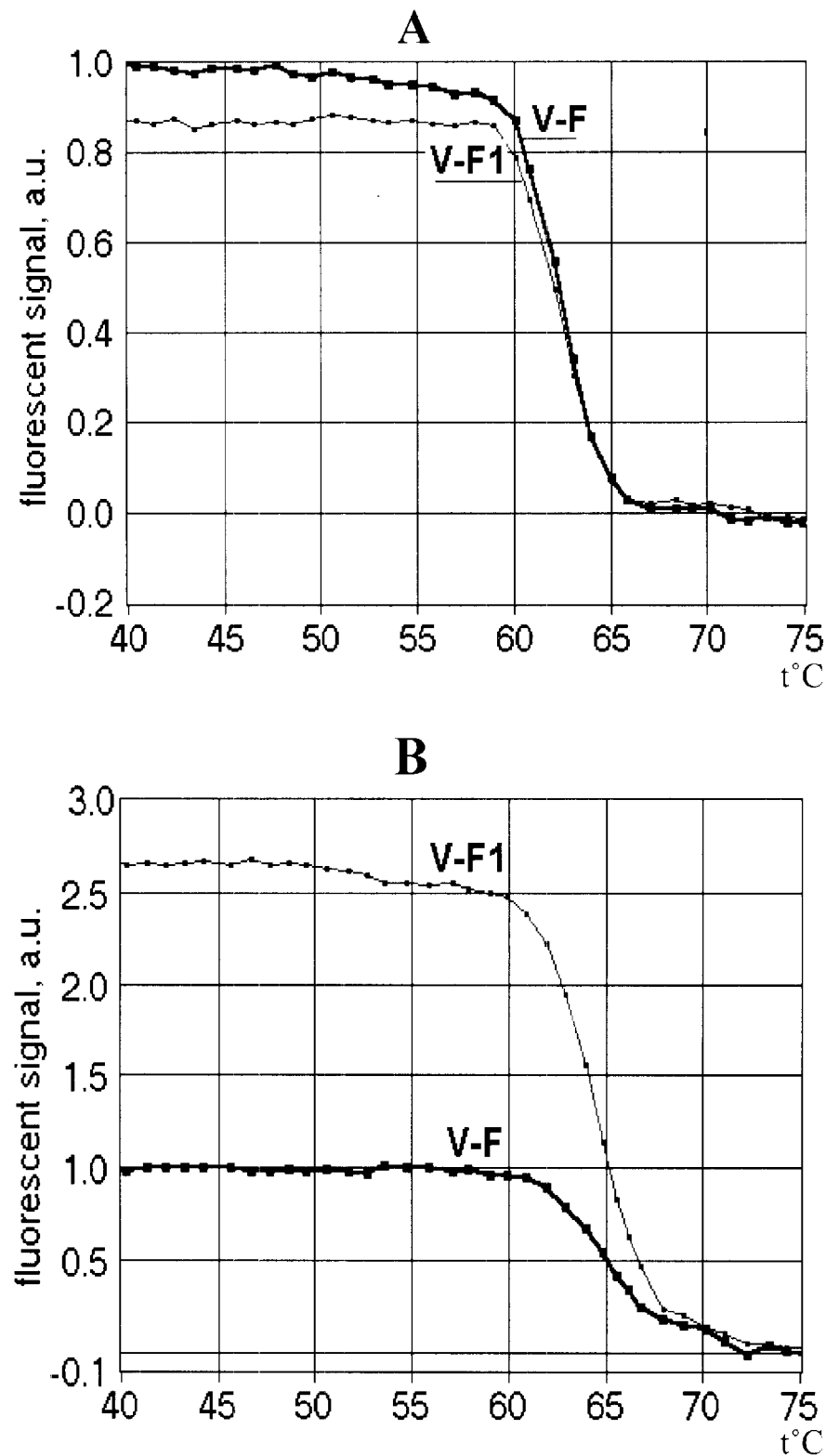

FIG. 21 shows melting curves of duplexes formed between extended (as a result of PCR) immobilized froward terminal brcal-F (continuous line) or internal brcal-F1 (dotted line) primers and flourescent internal (for the PCR amplified region) probe brcal-P1 (A, left graph) or fluorescent reverse primer brcal-R (B, right graph) measure in relat-time under fluorescent microscope.

Figure 22:
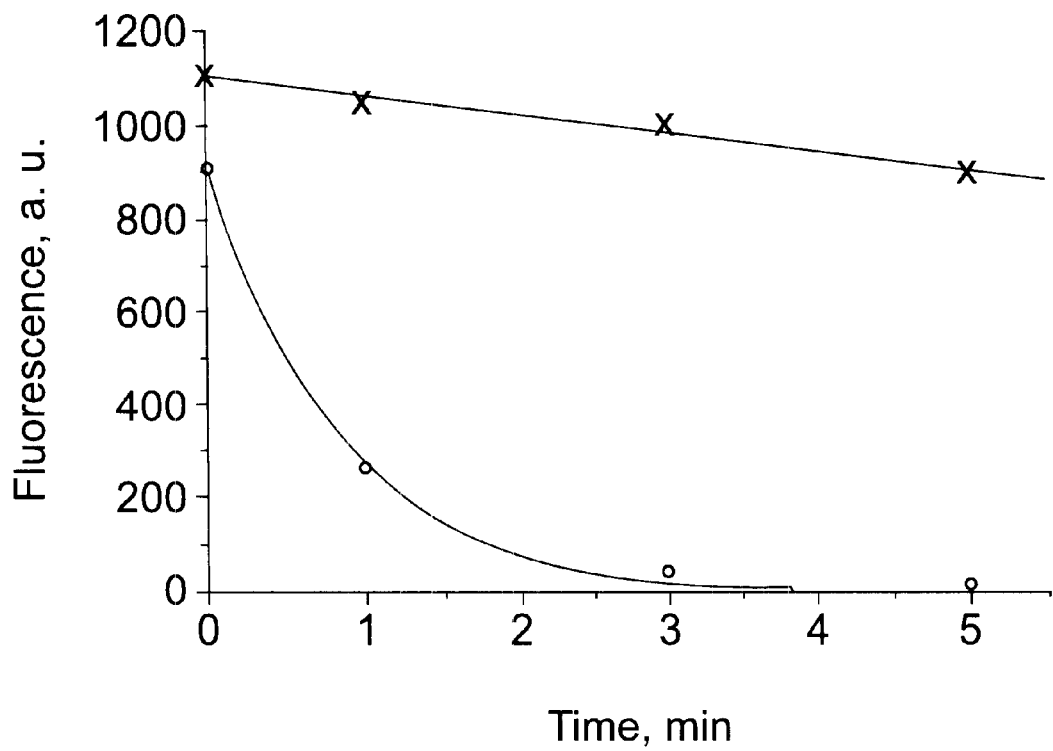

FIG. 22 shows cleavage and release of an immobilized chimeric oligodeoxyribonucleotide containing ribouridine region, which is being digested by ribonuclease A. The chimeric oligonucleotide 3'-dT-(rU)2-(dT)10-5' was immobilized within a gel pad of a microchip and hybridized with fluorescently labeled complementary 10-mer 3' Texas Red-(dA)10-5.

DETAILED DESCRIPTION OF THE INVENTION

PCR amplification is performed using gel immobilized oligonucleotides (microchips). In an embodiment one of each pair of PCR primers is immobilized within a separate microchip polyacrylamide or porous gel pad.

The on-chip PCR amplification has been shown to be a rapid, inexpensive, and powerful tool to detect specific genes, for example, those responsible for bacterial toxin production and drug resistance, as well as to reveal point nucleotide mutations.

The procedures of the invention allow concurrent amplification over (outside of) and within gel pads, as well as a modification in which the amplification occurs only within gel pads surrounded by oil. These amplification procedures were applied to amplify and identify a number of toxin genes, genes carrying resistance to the antibiotic ampicillin, human genomic bracl genes and other genes. A base polymorphism analysis was also performed by on-chip amplification. Procedures for enzymatically releasing and activating the gel-immobilized primers were developed for their further application in on-chip amplification. Polyacrylamide and newly developed, more porous, polyacrylamide gels were shown to be efficient in on-chip amplification.

The Micro Array of Gel Immobilized Compounds on a Chip (MAGIChip™) provides a suitable vehicle for combined amplification and detection of nucleic acid molecules. In the MAGIChip™, polyacrylamide gel pads containing immobilized oligonucleotides have volumes ranging from pico- to nanoliters. The pads are spaced with a hydrophobic glass surface that prevents the exchange of solutions between them. These gel pads were used as micro test-tubes in a number of chemical and enzymatic reactions, including oligonucleotide immobilization (e.g. Proudnikov et al., 1998), phosphorylation/ligation (Dubiley et al., 1997) and DNA polymerase reactions, such as single base extension (Dubiley et al., 1999).

The invention provides a general multipurpose type of microchip. Over/on chip amplification and its allele specific variation may be integrated on one MAGIchip with real time monitoring of the reaction kinetics, highly sensitive and selective detection of the amplified products by their hybridization with specific immobilized probes, and identification of genetic variants and mutations. These PCR and parallel hybridization procedures are performed for 2 hours with as little as $10^2$ DNA molecules. Over/on biochip PCR amplification for a few cases are shown in the examples: identification of bacterial toxin genes as well as genes and genome mutations responsible for bacterial drug resistance. However, this approach shows promise for being easily extendable to many other practically important tasks by means disclosed herein.

Microchips (e.g. MAGIChips™) perform multiplex on-chip PCR amplification of DNA molecules using microarrays containing immobilized and non-immobilized primers. This capability enables the microchip to amplify a large number of individual DNA sequences using a large number of amplification primers and to detect the products of these reactions.

There are several embodiments of PCR amplification on a microarray of gel-immobilized primers (microchip). For the simplest application of the methods, only one primer is immobilized within the gel pad, and both primers (one having an identical nucleotide sequence to the immobilized primer, and the other matching the nucleotide sequence from the opposite side of the amplified DNA fragment) were in the PCR amplification solution. Similar sets of primers, two (forward and reverse) in solution and one (forward) immobilized within an individual gel pad, were used to analyze different genetic regions such as *M. tuberculosis* rpoB gene, Anthrax toxin genes, Shiga and Shiga-like toxin genes and β-lactamase genes. One of a pair of PCR primers was immobilized inside a separate microchip polyacrylamide porous gel pad of 0.1×0.1×0.02 (0.04) mm in size and 0.2–0.4 nl in volume. The amplification was carried out simultaneously both in solution covering the microchip array and inside gel pads. Each gel pad contained the immobilized forward primers, while the fluorescently labeled reverse primers as well as all components of the amplification reaction diffused into the gel pads from the solution. To increase the amplification efficiency, the forward primers were also added into the solution.

The amplification is carried out in a hybridization chamber solution outside of the microchip as well as within each microchip gel pad. Both forward and fluorescently labeled reverse primers are utilized in solution. Each gel pad contains an immobilized forward primer or an internal primer whereas a second, reverse primer as well as all components of the amplification reaction diffuse into the gel pads from the solution.

The kinetics of amplification was measured in real time in parallel for all gel pads with a fluorescent microscope equipped with a CCD camera. The accuracy of the amplification was assessed by using the melting curves obtained for the duplexes formed by the labeled amplification product and the gel-immobilized primers during the amplification process; alternatively, the duplexes were produced by hybridization of the extended immobilized primers with labeled oligonucleotide probes.

An immobilized primer has restricted flexibility. The use of primers detached from the gel matrix (at least one primer of the pair) significantly improved the PCR amplification in the order: 2 detached primers>1 detached and 1 immobilized>2 immobilized primers.

Subsequently, PCR fragments enter the gel, hybridize to the immobilized oligonucleotides, and additional cycles of PCR are carried out within the gel elements themselves. PCR amplification is carried out by 20–40 temperature cycles in parallel, in the solution above the microchip gel pads and within the gel pads, or, only within the gel pads. The monitoring of the amplification within the microchip is carried out in real-time by measuring the increase in the fluorescence within the gel pads. This fluorescence appears as a result of the formation of labeled duplexes immobilized within the pad and/or by hybridization of an extended, immobilized primer with another fluorescently labeled primer in solution. Alternatively, the amplification can be detected and assessed quantitatively by the hybridization of the extended immobilized primer with a specific fluorescently labeled probes to form gel immobilized duplexes. The specificity of the hybridization can be additionally tested by measuring the melting curve kinetics of the duplex. The melting curve of the duplex is measured by registration of the decrease in fluorescence intensity of the labeled probe, hybridized to the immobilized, extended primer, as a function of increased temperature.

The melting curve kinetics allow confirmation that the correct region of DNA was amplified. Both the location of the melting curve at the range of high temperature and the sharpness of the curve itself are indications of the high specificity of the duplex formation and thus of the specificity of the PCR amplification. Curves that display a sharp drop in double-stranded regions with a small change in temperature indicate sequences that closely match the fluorescently labeled probe.

In an embodiment, the gel pads in the microchip are covered with oil. The microchip is then placed onto a temperature-controlled stage and thermocycling of the microchip allows PCR amplification of the genomic region of interest to take place.

Covering the gel pads with oil allowed amplification to be carried out within individual gel pads. This requires that each gel pad be supplied with both the specific forward and reverse primers, but one of them should be unattached to the gel. This requirement was satisfied by initially attaching both primers to the gel within a pad. However, one primer was detachable; i.e. the primer contained ribonucleotide residues within the 5'-terminal part of the oligonucleotide. The treatment of this immobilized detachable primer with ribonuclease breaks phosphodiester bonds at the ribonucleotide residues and releases the primer into the interior of the pad. Ribonuclease does not interfere with DNA polymerase reaction and thus, need not be removed for the following amplification. A number of commercially available ribonucleases exhibit different nucleotide specificities. For example, ribonuclease A, Barnase and guanilo ribonuclease demonstrate specificity to pyrimidine, guanine, or all four ribonucleotides, respectively. The incorporation into the primers of these ribonucleotide residues enables release of different primers in a specified order by using corresponding ribonucleases. The incorporation of the ribonucleotides into the 3'-terminal position would cause the appearance of a 3'-phosphate group and the inactivation of the primer upon the ribonuclease digestion. Such a primer can be reactivated upon dephosphorylation with phosphatase.

A fragment of a single copy gene (human bracal) contained in $10^5$ copies of genomic DNA was amplified under oil and detected within an individual gel pad. This demonstrated the high sensitivity and the efficiency of the procedure. The use of such amplification combined with successive enzymatic release, inactivation and activation of the microchip primers enables amplification, detection and nucleotide polymorphism analysis to be performed simultaneously for hundreds and thousands of human genes and genes of more simple bacteria and viruses.

Amplification within the microchip gel pad is less effective under oil than when the same PCR reagents are in solution because of limited reagent supplies within the tiny gel pad. By using detachable primers and special porous gel for PCR under oil, amplification efficiency was significantly improved. At least one primer should be immobilized, for use at the end of PCR amplification analysis to hybridize to and detect the created PCR product.

Amplification of the initial DNA sample (genomic, plasmid or fragmented genomic cDNA) using the methods of the present invention was started in solution in the environment (chamber) over the microchip and then proceeded in parallel, with short amplified fragments [amplicon DNA or amplicons] in solution outside (over) the gel pads of the microchip as well as within the gel pads of the microchip. Forward primers and one reverse primer were present in solution, and only one forward primer was immobilized within an individual gel pad for each amplified region. Amplification reactants, including the solution-amplified short DNA fragment, the reverse primer, and DNA polymerase, rapidly diffused from the solution into the tiny gel pads, where amplification occurred within the gel pads as well.

Diffusion of the reaction components into the standard polyacrylamide gel slowed down the reaction and restricted the size of DNA by 150–200 base pairs. A more porous gel was developed with the aim of facilitating diffusion of longer DNA (>200 bp) into the gel. Both gels were accessible to globular proteins of about 100,000 Daltons in size. PCR amplification of longer DNA fragments occurred mostly close to the surface of the standard gel but spread smoothly in the whole volume of porous gels (see the distribution of fluorescently labeled duplexes on FIG. 10). A microchip based multiplex amplification was carried out with many primers to identify the rpoB gene mutations, and the primers did not interfere with each other when immobilized within different gel pads.

Several PCR primers were developed and employed for practice of the invention, in particular the oil method. The two general types include: 1) primers which are immobilized onto gel pads on a microchip and are active as PCR primers immediately after immobilization, and 2) immobilized primers which are modulated, which means that their activity as PCR primers can be changed by a separate treatment after immobilization. The modulated primers are particularly suited for the oil covered gel pads.

There are three subtypes of modulated primers. First, releasable, that is detachable (temporarily immobilized) primers, are oligonucleotides that contain an oligoribonucleotide (RNA) linker incorporated into the 5'-terminal position of an oligodeoxynbonucleotide (DNA) primer that is immobilized onto the microchip gel pads, and that can subsequently be detached from the gel-matrix by treatment with a ribonuclease. Upon treatment with a specific ribonuclease enzyme, the primer splits at the ribonucleotide residues and is released. Another variation of a detachable primer is a primer with a S'-terminal gel linker that contains a cys vicinal deoxy group

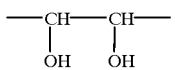

which can be split in the middle upon treatment with sodium peziodate ($NaJO_4$). Second, inactivatable (temporarily active) primers, are immobilized oligonucleotides that can be inactivated. These primers contain, for example, at least one oligoribonucleotide sequence in the middle or close to the 3' terminal position of the oligodeoxyribonucleotide primer. Upon treatment with a ribonuclease, these inactivatable primers are cleaved at the ribonucleotide sequence and inactivated. Either the fragments are incapable of hybridization, they are removed by washing, or the fragment is left with a phosphate group at its 3' hydroxylend.

Finally, activatable (temporarily inactive) primers are primers that need to be activated in order to serve as primers. For example, one activatable primer contains a phosphorylated 3'-terminal; the 3' phosphate prevents the primers from participating in the PCR. However, this phosphate group is removed by treatment with a phosphatase enzyme, thereby "activating" the primer which then participates in PCR.

Use of immobilized, detachable, activatable, and inactivatable primers have been explored. The successive application of PCR amplification followed by analysis of amplified DNA after its hybridization with (inner) immobilized primer, by performing primer extension, single base primer extension or ligation detection reaction for identifying specific DNA sequences and analyzing nucleotide polymorphisms in DNA.

A set of immobilized (including sequentially activated, inactivated or detached) primers within a single gel pad has many other applications. For example, their successive release, activation and inactivation can also be used to carry out nested primer amplifications by successive rounds of amplification, the activation of sets of interior forward or reverse primers that narrow the region of interest, to be amplified. Polymorphism analysis by single base extension of the amplified DNA can also be performed.

In one embodiment, a microchip is prepared with immobilized PCR primers complementary to a region or sequence of interest in a genomic DNA or RNA (cDNA). The oligonucleotides immobilized on the chip include oligonucleotides complementary to the boundaries of the DNA region of interest, or complementary to interior regions. A chamber is formed on the slide containing the microchip so that one or more of the following compositions could be added to the chamber: a mixture of fragmented genomic DNA or cDNA, primers, nucleotides, nucleases such as ribonucleases, DNA polymerase enzyme, at least one fluorescently labeled oligonucleotide probe, which is complementary to one of the products expected to be generated by the PCR reaction, and the necessary co-factors for the PCR reaction. One or more of the immobilized primers can be detachable, inactivatable or activatable.

Enzymes such as phosphatases and additional ribonucleases are added at appropriate times during the PCR process, activating, inactivating or detaching PCR primers. It is possible that initially the DNA is amplified only in the liquid phase above the gel elements of the microchip. However, the initial PCR products then diffuse into the gel pads and are amplified via the primers immobilized thereon.

Use of microchips containing sequentially controlled, gel-immobilized oligonucleotide primers for combinatorial PCR amplification combined with PCR product detection provides essential advantages over other forms of PCR. The capacity of the gel pads for immobilization exceeds the capacity of solids, such as a glass surface, by two orders of magnitude. Gel-immobilized compounds are in a more homogeneous water environment and therefore they are more accessible for interaction with enzymes as compared with solid phase-immobilized compounds. Immobilization in gel of both forward and reverse primers for a PCR reaction appears to restrict the flexibility of the DNA duplex fixed at both ends of these two primers, and significantly inhibits amplification. Therefore, for the present invention only one primer was immobilized in the gel pads of the microchip, whereas the others remained in solution, and either detached from the gel during hybridization, or were combinatorially activated/inactivated as directed by the particular application.

In addition, by using a new structure of microchip gel pad, one in which a hole is formed inside the gel pad, the standard gel pad possesses a larger volume of aqueous solution, providing an increase in the reagents available for the PCR enzymatic reactions during PCR under oil. This structure is formed by blocking the uv radiation over the center of the gel pad during photo-polymerization.

EXAMPLES

Example 1

Amplification in the Microchip Chamber

Figure 1:
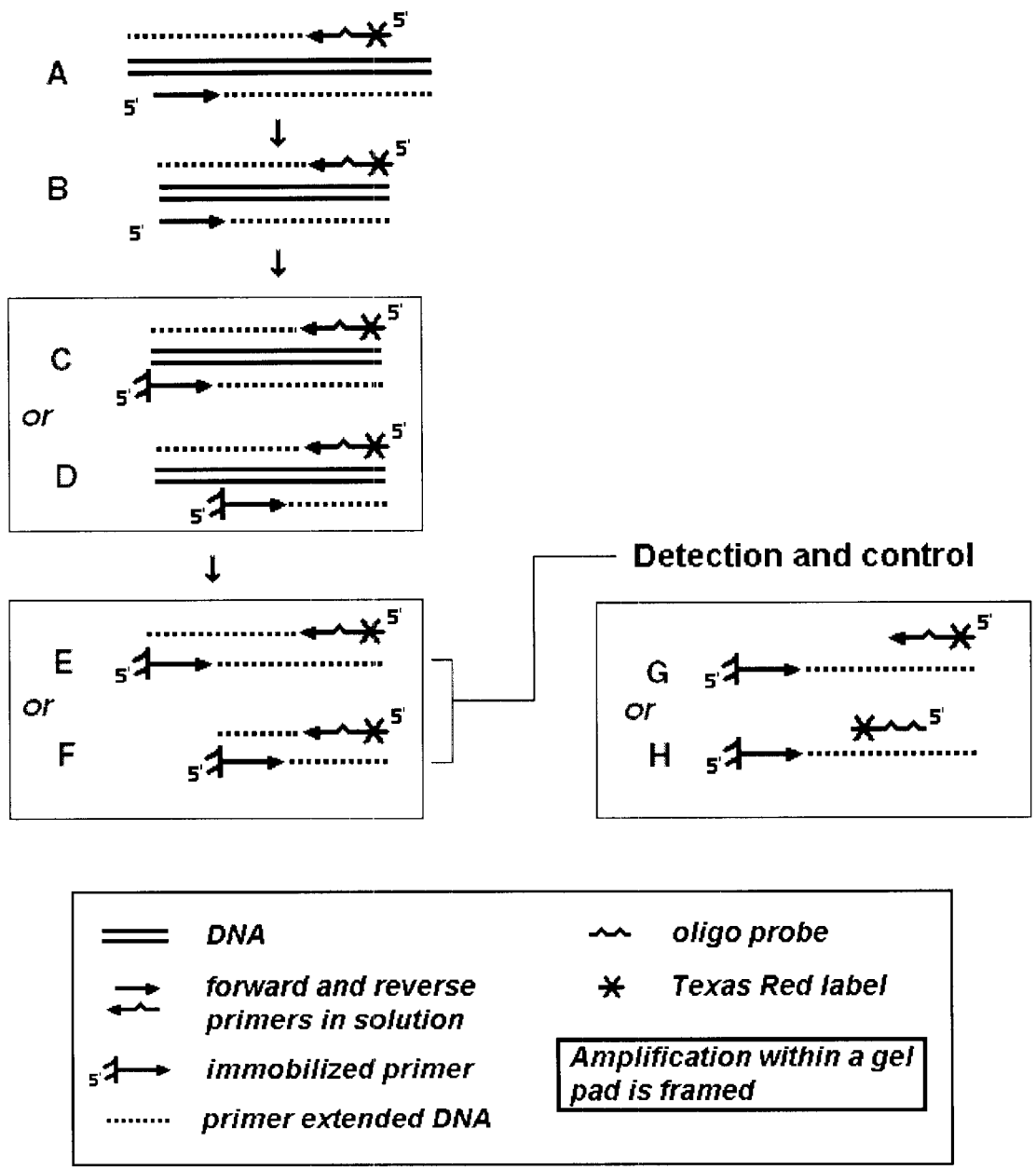
FIG. 1 illustrates schematically PCR amplifications outside and within oligonucleotide microchips. The initial DNA was first amplified in solution over a microchip (A); the short fragment was further amplified over (B); and within the microchip gel pads on immobilized forward (C) or internal (D) primers; labeled duplexes were formed by hybridization of the extended immobilized primers with the amplified fluorescently labeled complementary strand (E, F) and were monitored in real time with a fluorescent microscope; the specificity of the reaction was tested by hybridization of the extended immobilized primers with the labeled reverse primer (G) or internal probe (H); amplifications inside the gel pads on the immobilized primers are boxed.

The scheme showing parallel amplification in solution and within (inside of) gel pads is given in FIG. 1. The solutions of DNA, forward (F) and reverse (R) primers (FIG. 1A), and all other components necessary for amplification were placed over the oligonucleotide microchip in a hybridization chamber. The reverse primers were fluorescently labeled with Texas Red, shown by *. The microchip contained gel-immobilized forward primers that were either the same as those in solution, or were complementary to an internal region (internal primer, IP) of the amplified DNA (FIGS. 1, C and D). The large size of the initial DNA template limited its diffusion into the gel. Therefore, the initial rounds of amplification were carried out in solution (FIG. 1A). A short amplified DNA fragment (FIG. 1B), the labeled reverse primer, the DNA polymerase, and all other components of the amplification buffer diffused into the gel pads of the microchip from the solution in the hybridization chamber. The subsequent rounds of amplification occurred both in the solution (FIG. 1B) and within the gel pads and caused extension of the immobilization forward terminal (FIG. 1C) or internal (FIG. 1D) primers. Amplification was monitored with the fluorescence microscope by measuring the hybridization signal of the extended immobilization primers with the fluorescently labeled amplified upper strand of the DNA fragment in each gel pad of the microchip (FIGS. 1, E and F). Alternatively, internal probes could be labeled through the 3'-end which prevented its extension during the amplification procedure (FIG. 1H). The labeled inactivated probe could be added to the unlabeled forward and reverse primers in the reactions shown in FIGS. 1, A, B, and D; and its hybridization with the extended forward primer could be used to monitor the amplification kinetics.

To test the specificity of on-chip PCR amplification using the microchip, the DNA duplexes were dissociated at high temperature, and the fluorescently labeled strands were washed off the gel pads. Then the remaining immobilized extended primers were hybridized with the added fluorescently labeled reverse primer (FIG. 1G) or with an internal oligonucleotide probe (FIG. 1H). The specificity of hybridization, and thus of amplification, was controlled by monitoring the melting curves of the duplexes formed within the gel pads by the fluorescence microscope.

The experiments described below demonstrate some practical applications of the microchip amplification.

Example 2
Detection of Anthrax Toxin Genes

PCR improvement was achieved through the development of PCR amplification on a Microarray of the Gel-Immobilized Compounds on a Chip (MAGIChip™). The MAGIChip™ had an array of polyacrylamide-based gel pads of the size of 0.1×0.1×0.02 (or 0.04) mm and contained different immobilized oligonucleotides. The microchip gel pads served as microtest tubes, 0.2–0.4 nl in volume, and have been used in a number of chemical and enzymatic reactions such as immobilization of oligonucleotides and DNA through covalent bonds, DNA ligation and DNA polymerase extension of immobilized oligonucleotides. A new procedure for bacterial analysis combines PCR amplification on MAGIChip™, multiplex allele-specific amplification, and detection of amplified fluorescently labeled products with a fluorescent microscope. PCR analysis was also carried out in real time to monitor the kinetics of the reaction.

The amplicons containing fragments of the lethal factor (lef) gene and the protective antigen (pag4) gene were used in the detection of the anthrax toxin genes. Two forward primers, lef-F and pag4-F, as well as two fluorescently labeled reverse primers, lef-R and pag4R (see Table 1), for these two genes were present in the amplification mixture containing either lef or pag4 amplicons. A standard polyacrylamide gel microchip contained forward primers, lef-F and pag4-F, for these genes immobilized separately within different (separate) gel pads. Amplification led to the formation of duplexes between the immobilized extended primers and the amplified labeled upper (complementary) strand of the DNA fragments (FIG. 1C). FIGS. 2A and B show the kinetics of amplification of the lef and pag4 fragments.

Figure 2:
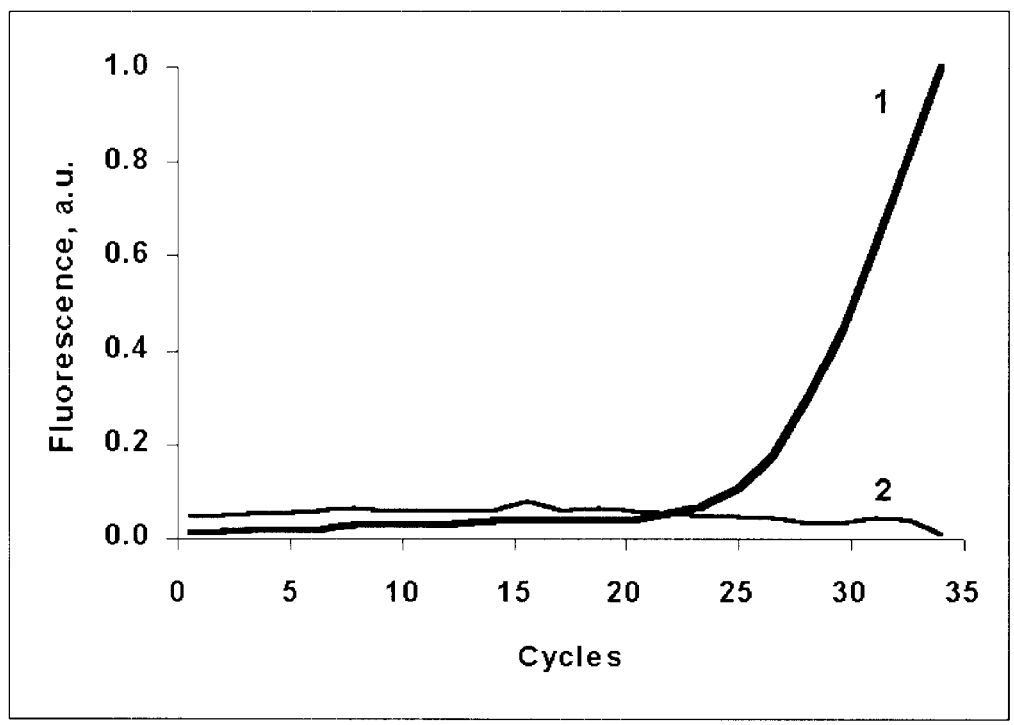
FIG. 2 demonstrates amplification of anthrax toxin gene fragments.
Figure 2:
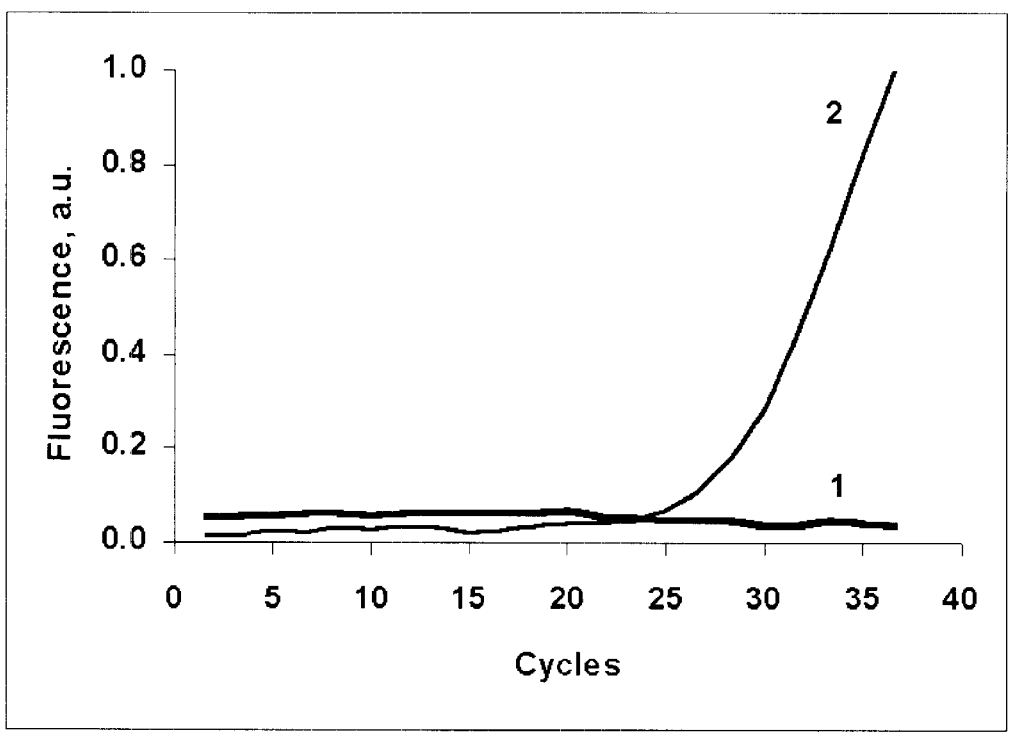

FIG. 2 shows amplification of anthrax toxin gene fragments. The microchip gel pads contained immobilized forward lef-F (see Table 1) or pag4-F primers. The PCR amplification solution contained unbound forward lef-F and pag4-F primers, labeled reverse lef-R and pag4-R primers, and either lef or pag4 amplicons. The kinetics of amplification were monitored in real-time as the accumulation of fluorescently labeled duplexes formed by the extended immobilized lef-F primer (curve 1) or pag4-F primer (curve 2) and the complementary DNA strands of either lef (A) or pag4 (B) amplicons (see also FIG. 1C for the scheme of the process).

The accumulated fluorescence signal within the gel pads was measured in real time and in parallel for all microchip elements. Exponential amplification of each DNA template was observed only for the gel pads containing appropriate pairs of the gene fragment and immobilized primers, upon the $23^{rd}$ and $25^{th}$ cycle for lef and pag4 DNA, respectively. No significant fluorescence was detected for the pads containing non-corresponding (inappropriate) primers. The average amplification coefficient in each cycle was about 1.89, as determined by calculating the increase in the fluorescence intensity averaged over several cycles within the logarithmic phase of the amplification curve. The size of the DNA fragments amplified in solution over the chip was found to correspond to the expected length as measured by gel electrophoresis in 2% agarose gel.

The specificity of on chip amplification was evidenced by hybridization of the extended immobilized pag4-F primer with oligonucleotide probe pag4-P specific for the internal

TABLE 1

Primers Used For Detection Of Anthrax Toxin Genes

| Oligonucleotide | Positions* | Sequence 5' → 3' | $T_{an}°$ C.** |
|---|---|---|---|
| lef-F | 1255 | CCCTTGATAATATCTTACC (SEQ ID NO:1) | 51 |
| lef-R | 1153 | GATATGAACCCGTACTTG (SEQ ID NO:2) | 51 |
| pag4-F | 1931 | CAAGTTCCCAGGGGTTACTAGG (SEQ ID NO:3) | 58 |
| pag4-R | 2178 | CACTTCTTGGTCATCTACCCAC (SEQ ID NO:4) | 58 |
| pag4-P | 2155 | TTGTTACATGATTATCAGCGGAA (SEQ ID NO:5) | 58 |

*The column indicates the 5' nucleotide position number of the corresponding oligonucleotide (primer) of the gene encoding sequence counting from the 5'-terminus of the gene encoding sequence. F-forward, R-reverse, primers, respectively; P- hybridization probe.
**Annealing temperature, $T_{an} = T_m(4 \text{ to } 6)°$ C. Melting temperature was calculated with Williamstone Software. by the nearest neighbor method.

region of the pag4 amplicon (see FIG. 1H). As can be seen from FIG. 3, the melting curve of the formed duplex is sharp and is located in the range of expected increased temperatures which confirms a high specificity of amplification. The sharp decrease of the fluorescent signal within the narrow temperature range points out to the high cooperative interaction process, which indirectly confirms full complementarity of the probe and the amplified DNA.

Figure 3:
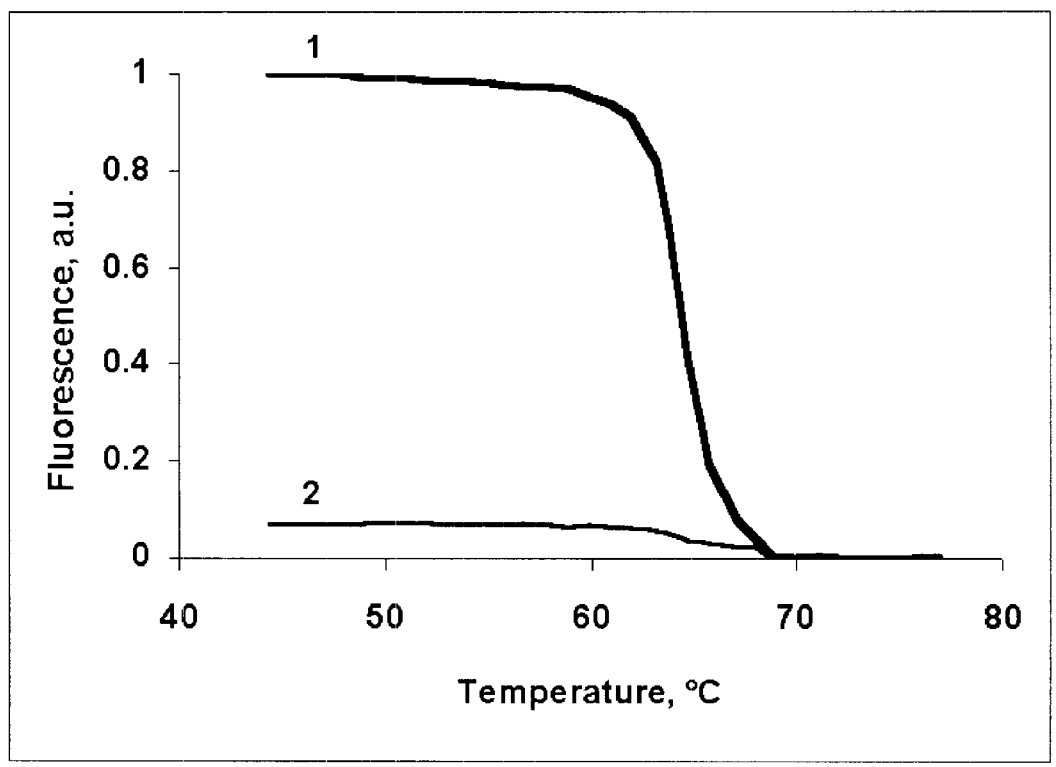
FIG. 3 shows melting curves of the duplex containing extended pag4 microchip primer and pag4 internal labeled probe.

FIG. 3 presents melting curves of the duplex containing extended pag4 microchip primer and pag4 internal labeled probe. After PCR amplification of the pag4 amplicon (see FIG. 2B), microchip duplexes were dissociated and lef-F (curve 2) and pag4-F (curve 1) extended immobilized primers were hybridized with labeled oligonucleotide pag 4-P probe specific to the pag4 amplicon (see FIG. 1H). Melting curves were monitored in real-time with the fluorescence microscope for both gel pads.

Figure 4:
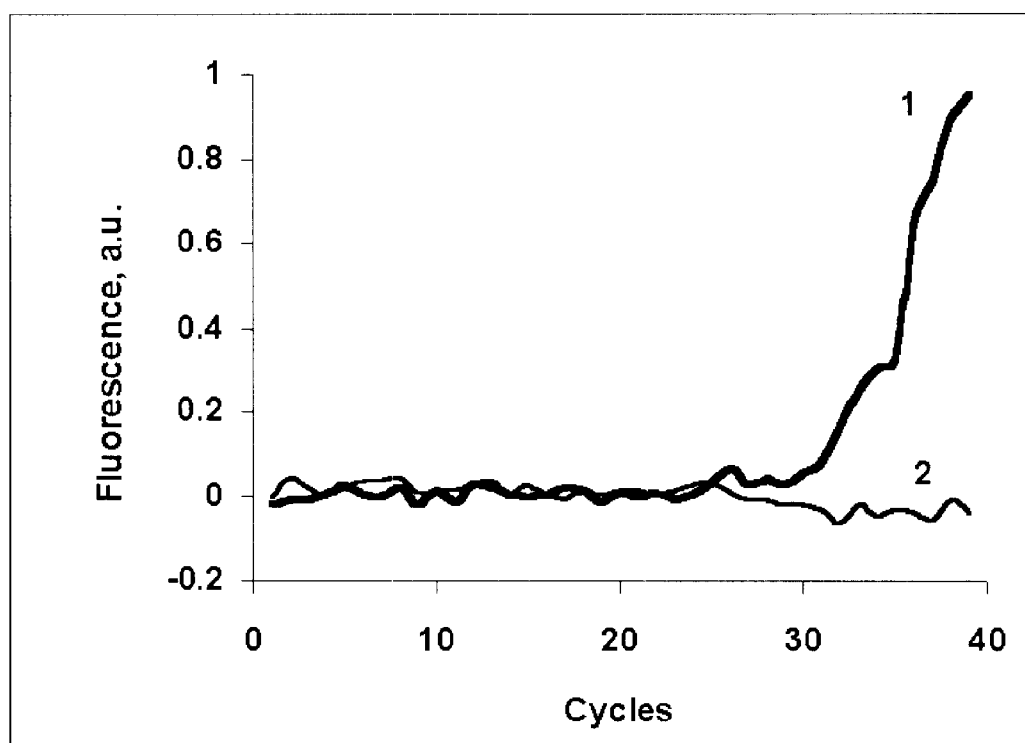
FIG. 4 shows results of monitoring of microchip amplification of the pag4 gene fragment with internal labeled probe.

Alternatively, the kinetics and specificity of amplification were tested by performing the reaction in the presence of unlabeled forward and reverse primers (FIGS. 1A, B and C) and a 3'-labeled inactivated probe for an internal region (FIG. 1H) of the amplicon. FIG. 4 shows monitoring of the pag4 amplification by measuring hybridization of the fluorescently labeled internal pag4 probe, pag4-P, with the extended immobilized forward primer pag4-F. The pag4-P probe contained a Texas Red label at the 3'-terminal position and was therefore inactive in PCR amplification. Exponential growth in fluorescence was observed upon the $26^{th}$ round of amplification, that is by 2–3 rounds later than in a similar experiment performed in the absence of the internal probe (FIG. 2A). The inhibition could be accounted for by the competition for the lower strand between the inactive probe and the active lower primer during amplification. In addition, the efficiency of hybridization between the extended immobilization primer and the shorter internal probe could be lower as compared with the much longer upper DNA strand (FIG. 1: compare E and H).

FIG. 4 shows results of monitoring of the microchip amplification of the pag4 gene fragment with an internal labeled probe. The pag4 amplicon was amplified as in FIG. 2B except that primers lef-R and pag4-R were unlabeled. A 3' Texas Red-labeled probe, pag4-P, for internal amplicon region, inactive as a primer, was added to the reaction mixture (FIG. 1H). The fluorescence signal increased in the gel pads containing pag4-F (curve 1) but not lef-F (curve 2) primers.

Example 3

Detection of β-lactamase Gene

Figure 5:
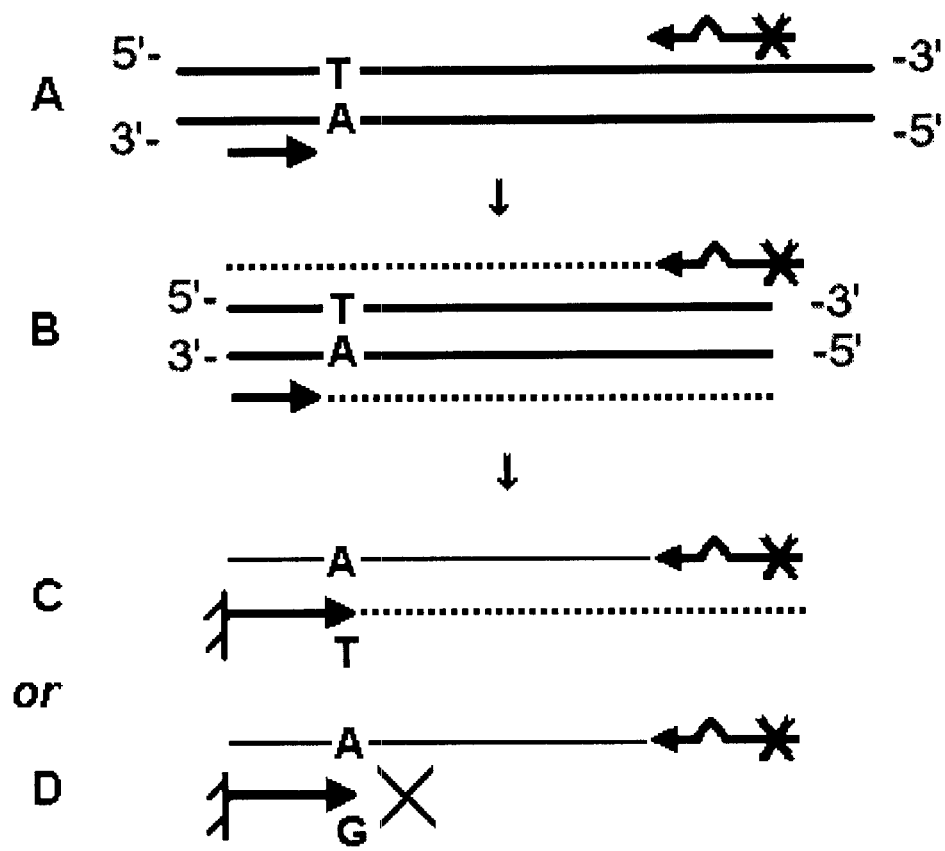
FIG. 5 shows amplification of the ampicillin resistance bla-gene.

The combined amplification over (outside) and within (inside) standard polyacrylamide gel pads was also used for identification of the beta-lactamase (bla) gene in plasmid pUC18 carrying bacterial resistance to ampicillin. FIG. 5 shows the microchip chamber amplification of the ampicillin resistance bla-gene. (FIG. 1 C and D) The PCR amplification solution contained forward primer bla-F, labeled reverse primer bla-R, and plasmid pUC18. Different gel pads of the microchip contained either forward terminal primer bla-F (curve 1), the same as in solution, or different internal primer bla-FI (curve 2).

TABLE 2

Primers Used For Detection Of Lactamase B-Gene

| Oligonucleotide | Positions* | Sequence 5'→3' | $T_{an}$° C.** |
|---|---|---|---|
| bla-F | 2656 | CCGCCTCCATCCAGTCTATT (SEQ ID NO:6) | 58 |
| bla-R | 2748 | CTGTAGCAATGGCAACAACG (SEQ ID NO:7) | 58 |
| bla-FI | 2682 | TGCCGGGAAGCTAGAGTAAGTAGTT (SEQ ID NO:8) | 64 |

*The column indicates the 5' nucleotide position number of the corresponding primer, counting from the 5'-terminus of the gene encoding sequence. F-forward, R-reverse, and IF-internal forward primers, respectively.
**Annealing temperature, $T_{an} = T_m(4$ to $6)$° C. Melting temperature was calculated with Williamstone Software. by the nearest neighbor method.

FIG. 5 shows a comparison of the two variants of the amplification procedure (FIGS. 1C and D) carried out with immobilized primer, either the same forward primer as in solution over microchip (bla-F primer), or with the internal primer bla-Fl (Table 2). In the first variant (line 1 in FIG. 5), the same forward primer bla-F was present in solution and was immobilized within the gel pad. In the second variant (line 2 in FIG. 5), another forward primer bla-FI complementary to an internal region of the DNA fragment was attached to the gel. The use of the same primer in solution and for immobilization caused much higher amplification as compared with the use of different internal forward primers in solution and on the gel pad. However, the amplification in the second method provided higher accuracy of the procedure. This method can be compared in accuracy to nested primer amplification in which successive sets of internal primers are used to re-amplify the extended fragments generated in the previous amplification step. Nested PCR generally only work when the previous amplification step provides a substrate that contains the correct nucleotide sequence for the next round of hybridization and subsequent amplification.

Example 4
Detection of the Shiga Toxin Gene and Polymorphic (Nucleotide) Versions of this Gene Shiga (sht) and Shiga-like (slt) toxin genes differ by four point mutations. Therefore, detection of Shiga toxin gene and its discrimination from Shiga-like toxin gene should be performed in parallel with identification of the polymorphic nucleotides in at least one position. The T to G transversion at the $1648^{th}$ nucleotide of the sht and slt genes was selected for comparison.

TABLE 3

Primers Used For Detection of Shiga Toxin Gene

| Oligonucleotide | Positions* | Sequence 5' → 3' | $T_{an}$ ° C.** |
|---|---|---|---|
| sht-F(T) | 1619/1648 | T TTCTTTGTTATCTTTTCAGTTAATGTGGTT (SEQ ID NO:9) | 67 |
| slt-F(G) | 1619 1648 | G TTCTTTGTTATCTTTTCAGTTAATGTGGTG (SEQ ID NO:10) | 67 |
| sht-F | 1619 | TTCTTTGTTATCTTTTCAGTTAATGTGGT (SEQ ID NO:11) | 65 |
| sht-R | 1757 | TACCTCCTGATGAAATAGTCTGTAATGG (SEQ ID NO:12) | 67 |

*The first column indicates the nucleotide position number, counting from the 5'-terminus of the gene encoding sequence. The second column indicates the position of a mutated base. F-forward and R-reverse primers, respectively
**Annealing temperature, $T_{an} = T_{an}(4 \text{ to } 6)$° C. Melting temperature was calculated with Williamstone Software. by the nearest neighbor method.

Figure 6:
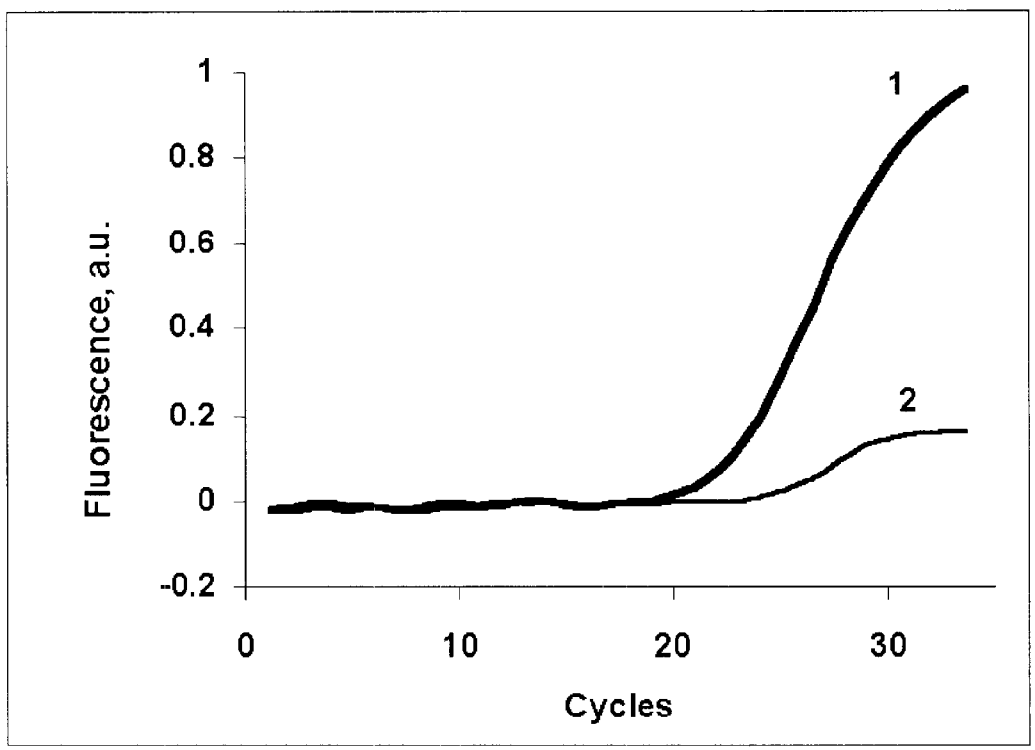
FIG. 6 illustrates schematically allele-specific PCR amplification of the Shiga toxin (sht) gene fragment and the discrimination of T-containing Shiga from G-containing Shiga-like (slt) toxin gene. A specific region of the sht gene was amplified from the plasmid PSHT23 in solution with forward primer sht-F and labeled reverse primer sht-R, which were complementary to both sht and slt genes. The microchip-immobilized two forward primers contained at the 3'-terminal position either T, sht-F(T) or G, slt-F(G), corresponding to T or G at position 1648 of sht or slt genes respectively.

Modification of the allele-specific PCR amplification was used to discriminate these mutations. The scheme of the experiment of allele-specific PCR amplification of the Shiga toxin (sht) gene fragment and the discrimination of T-containing Shiga from G-containing Shiga-like (slt) toxin gene is shown in FIG. 6.

A specific region of the sht gene was amplified from the plasmid pSHT23 in solution with forward primer sht-F and labeled reverse primer sht-R, which were complementary to both sht and slt genes. The microchip-immobilized two forward primers contained at the 3'-terminal position either T, sht-F(T) or G, slt-F(G), corresponding to T or G at position 1648 or sht or slt genes, respectively. The "X" indicates a blocked extension. See FIGS. 1 A and B, C and D for schematic diagram of the experiment.

The amplification solution contained unlabeled forward primer sht-F (Table 3), labeled reverse primer sht-R, and the pSHT23 plasmid. In the forward primer sht-F, the 3'-terminal nucleotide is positioned just before the polymorphic $1648^{th}$ nucleotide (FIG. 6A). Therefore, in solution amplification on these two primers should be similar for both genes. Two forward primers, sht-F(T) and slt-F(G), were immobilized within different pads of porous gel compound and corresponded to the sht-F(T) and slt-F(G), were immobilized within different pads of porous gel and corresponded to the sht or slt genes, respectively. They overlapped the polymorphic nucleotide by one base (FIG. 6B) and are derived from sht-F by extension of its 3'-terminal nucleotide with either T or G.

Figure 7:
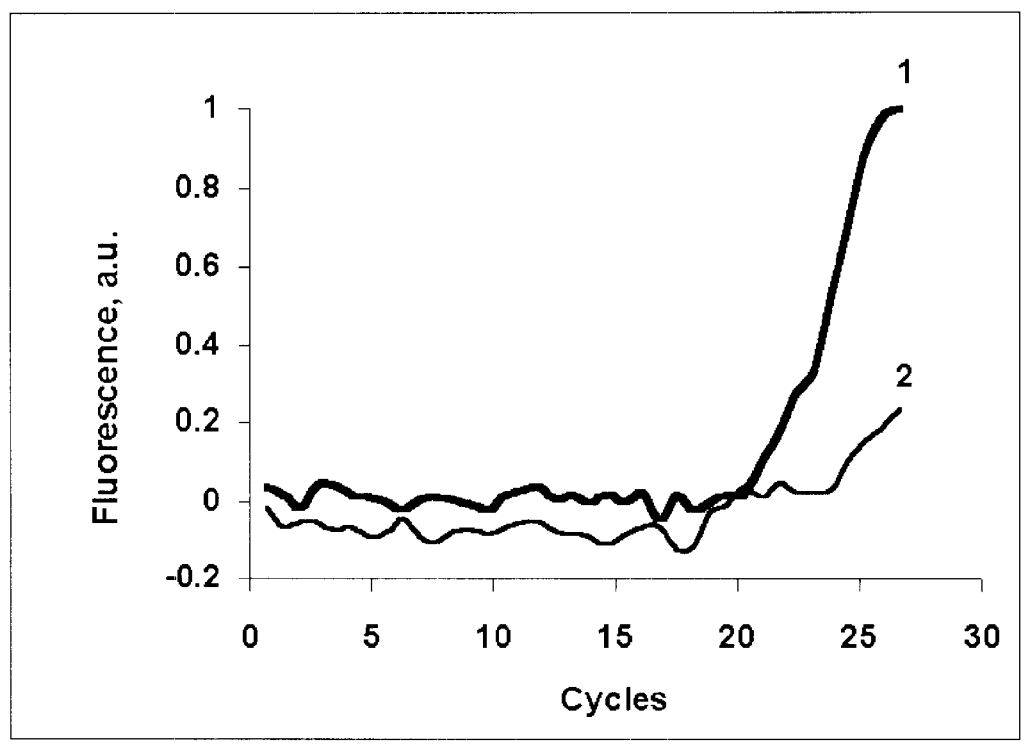
FIG. 7 illustrates allele-specific PCR amplification of the Shiga toxin gene fragment on immobilized sht-F(T) (curve 1) and slt-F(G) (curve 2) primers. (see also FIG. 6)

FIG. 7 shows the kinetics of amplification of the sht gene on two sht- and slt-immobilized primers. The amplification occurred much more efficiently on the fully complementary T-containing sht immobilized primer sht-F(T) (FIG. 6 C). The kinetics of amplification was monitored by hybridization of the fluorescently labeled upper (complementary) DNA strand with the extended primer. The Stoffel DNA polymerase fragment used in the reaction lacked exonuclease activity and was unable to extend efficiently the terminally mismatched slt immobilized primer slt-F(G) (FIG. 6D). Some fluorescent signal was still evident on the mismatched slt primer slt-F(G), which was probably due to its terminally mismatched hybridization with the amplified labeled upper sht DNA strand. Thus, the difference in the kinetics of extension of the microchip immobilized primers enables base polymorphism analysis to be performed in the course of gene identification.

Example 5
Identification of Rifampicin Resistant *M. tuberculosis* Mutations 39 identified rifampicin resistance mutations were localized within a short 81 bp region of the rpoB gene coding for the β-subunit of RNA polymerase.

TABLE 5

Primers Used For Detection Of Rifampicin Resistant Mutations

| Oligonucleotide | Positions* | Sequence 5' → 3' | $T_{an}$ °C.** |
|---|---|---|---|
| rpoB-F | 1275 | CGCGATCAAGGAGTTCTTCGGCACC SEQ ID NO:13 | 68 |
| rpoB-R | 1377 | CCCGGCGGTCTGTACGTGA SEQ ID NO:14 | 65 |
| rpoB-IF1A 5/1323 W | 129 | GCACCAGCCAGCTGAGACAATTCATGGAC SEQ ID NO;15 | 70 |
| rpoB-IF1B | 1295/1322 A→T | GCACCAGCCAGCTGAGACAATTCATGGt SEQ ID NO:16 | 70 |
| rpoB-IF1C | 1295/1321 G→T | GCACCAGCCAGCTGAGCCAATTCATGt SEQ ID NO:17 | 70 |
| rpoB-IF1D | 1295/1323 C→G | GCACCAGCCAGCTGAGACAATTCATGGAg SEQ ID NO:18 | 70 |
| rpoB-IF2A | 1308/1336 W | GAGCCAATTCATGGACCAGAACAACCCGC SEQ ID NO:19 | 70 |
| rpoB-IF2B | 1306/1336 C→A | CTGAGCCAATTCATGGACCAGAACAAC-CCGA SEQ ID NO:20 | 70 |
| rpoB-IF3A | 1310/1340 W | GCCAATTCATGGACCAGAACAACCCGCT-GTC SEQ ID NO:21 | 71 |
| rpoB-IF3B | 1310/1340 C→T | GCCAATTCATGGACCAGAACAACCCGCT-GTt SEQ ID NO:22 | 71 |
| rpoB-IF4A | 1323/1351 W | CCAGAACTACCCGCTGTCGTGGTTGACCC SEQ ID NO:23 | 71 |
| rpoB-IF4B | 1323/1351 C→T | CCAGAACTACCCGCTGTCGTGGTTGACCt SEQ ID NO:24 | 71 |
| rpoB-IF4C | 1323/1351 C→G | CCAGAACTACCCGCTGTCGTGGTTGACCg SEQ ID NO:25 | 71 |
| rpoB-IF4D | 1323/1351 C→A | CCAGAACTACCCGCTGTCGTGGTTGACCa SEQ ID NO:26 | 70 |
| rpoB-IF5A | 1325/1352 W | AGAACTACCCGCTGTCGTGGTTGACCCA SEQ ID NO:27 | 71 |
| rpoB-IF5B | 1325/1352 A→G | AGAACTACCCGCTGTCGTGGTTGACCCg SEQ ID NO:28 | 71 |
| rpoB-IF5C | 1325/1352 A→T | AGAACTACCCGCTGTCGTGGTTGACCCt SEQ ID NO:29 | 71 |
| rpoB-IF5D | 1325/1352 A→C | AGAACTACCCGCTGTCGTGGTTGACCCc SEQ ID NO:30 | 71 |
| rpoB-IF6A,7A | 1343/1367 W | GGTTGACCCACAAGCGCCGACTGTC SEQ ID NO:31 | 70 |
| rpoB-IF6B,7B | 1343/1367 C→T | GGTTGACCCACAAGCGCCGACTGTt(A-G) SEQ ID NO:32 | 70 |
| rpoB-IF6C,7C | 1342/1367 C→G | GGGTTGACCAACAAGCGCCGACTGTGT SEQ ID NO:33 | 70 |
| rpoB-IF6D | 1342/1367 C→G | GGGTTGACCAACAAGCGCCGACTGTgG SEQ ID NO:34 | 70 |
| rpoB-IF7D | 1342/1367 C→A | GGGTTGACCAACAAGCGCCGACTGTa(C-T) SEQ ID NO:35 | 70 |
| rpoB-IF8A | 1349/1373 W | CCCACAAGCTCCGACTGTAGGCGCT SEQ ID NO:36 | 71 |

TABLE 5-continued

Primers Used For Detection Of Rifampicin Resistant Mutations

| Oligonucleotide Positions* | Sequence 5' → 3' | $T_{an}$ °C.** |
|---|---|---|
| rpoB-IF8B | 1349/1373 T→C | CCCACAAGCTCCGACTGTAGGCGCc SEQ ID NO:37 71 |

*The first column indicates the nucleotide position number, counting from the 5'-terminus of the gene encoding sequence. The second column indicates the position of a mutated base. W-wild type base, F- forward, R- reverse, and IF- internal forward primers, respectively; P -hybridization probe.
**Annealing temperature, $T_{an} = T_m(4$ to $6)°$ C. Melting temperature was calculated with Williamstone Software. by the nearest neighbor method.

Multiplex allele-specific microchip PCR amplification with several immobilization primers was performed for the identification of some of these mutations. The scheme of these experiments (FIGS. 1, A, B, D, and F) was quite similar to those used for discriminating the Shiga and Shiga-like toxin genes (FIGS. 6 C and D). Genomic *M. tuberculosis* DNA isolated from pulmonary sputum was first amplified over a microchip in the hybridization chamber with the forward primer rpo-B-F and reverse primer 2poβ-R to produce a 123 bp fragment including the region of the mutations (FIG. 1A). The microchip contained 25 immobilized internal primers (Table 5). Among these, 16 corresponded to the mutations most often occurring in the Moscow region. The 3'-terminal nucleotides of these immobilized primers matched variable, mutated bases of the gene. Six of the other immobilized oligonucleotides corresponded to wild type sequences and were used as internal controls for mutant base detection. The labeled upper (complementary) strand of amplified DNA was hybridized with all multiplex primers of the microchip. However, only those primers that were complementary at their 3'-terminal position to the amplified DNA were efficiently extended with Stoffel DNA polymerase (FIG. 6C), and the reaction with the terminally mismatched duplexes was at least 5–10 times less efficient (FIG. 6D). The extended primers formed more stable duplexes upon hybridization with the labeled upper strand of the amplified DNA than the shorter unextended ones and they could be easily discriminated at the increased temperature.

Figure 8:
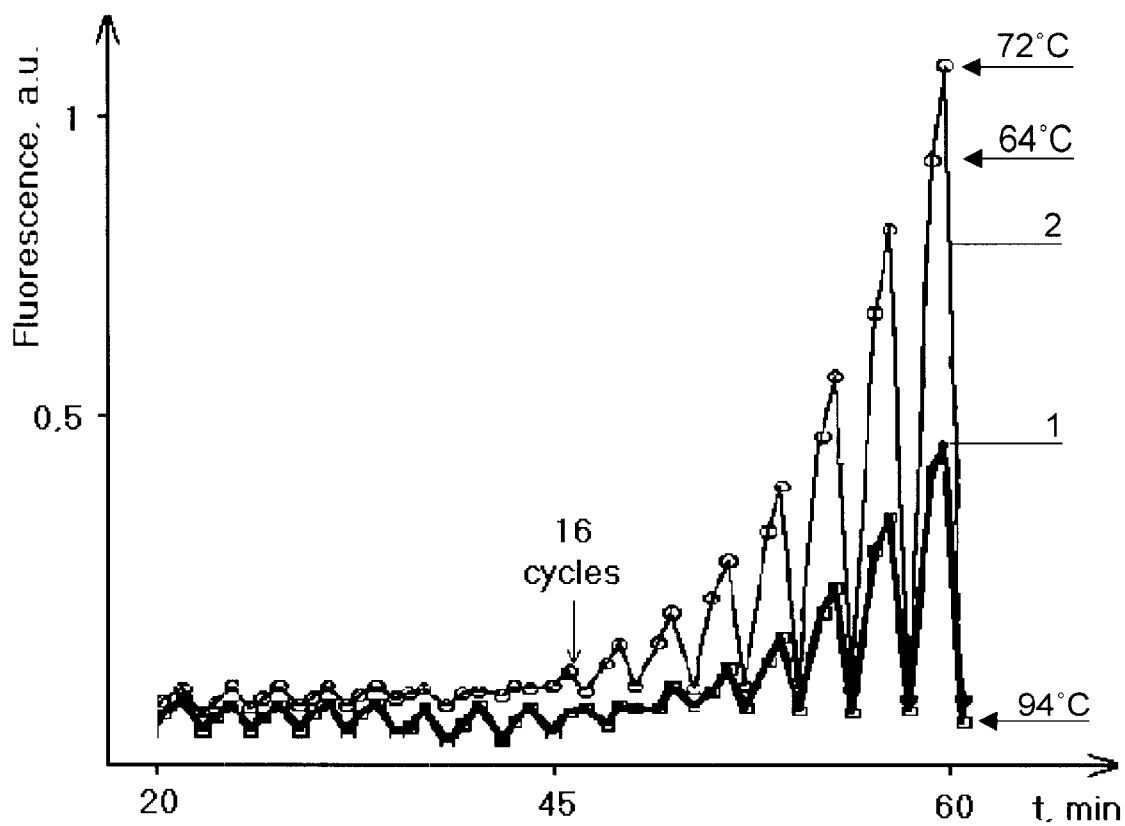
FIG. 8 presents results of monitoring of on-chip PCR amplification of the region of *M. tuberculosis* rpo B gene containing rifampicin-resistance mutations; the fluorescence measurements of the amplification of a mutated DNA from a clinical sample (sputum) were carried out in microchip gel pads 6A (curve 1) and 6B (curve 2), which contained the wild-type and C/T mutation primers, respectively; real-time kinetics measurements were carried out at the extension temperature 72° C. (upper points), annealing temperature 64° C. (middle points), and denaturation temperature 94° C. (lower points) of PCR cycles (for details see FIG. 9II and Table 1).

Short duplexes formed between amplified DNA and mismatch immobilized primers could be easily discriminated at increased temperature from long duplexes formed between amplified DNA and extended perfect match primers. The reaction kinetics were quantitatively monitored in real time at this temperature (the range of 72–85° C., dissociation step of amplification) under fluorescent microscope. The amplification kinetics of mutated genomic DNA was measured for the gel pads containing immobilized primer for the mutated (rpoB-IP6B, Table 5) and wild (rpo B-IP6A) strains and are shown in FIG. 8. FIG. 8 shows results of monitoring of the on-chip PCR amplification of the region of *M. tuberculosis* rpo B gene containing rifampicin-resistance mutations. The fluorescence measurements of the amplification of a mutated DNA from a clinical sample (sputum) were carried out in microchip gel pads 6A (curve 1) and 6B (curve 2) (see FIG. 9II) which contained wild-type and C/T mutation primers, respectively. Real-time kinetics measurements were carried out at extension temperature 72° C. (upper points), annealing temperature 64° C. (middle points) and denaturation temperature +94° C. (lower points) of the PCR cycles. For details, see FIG. 9II and Table 5.

Figure 9:
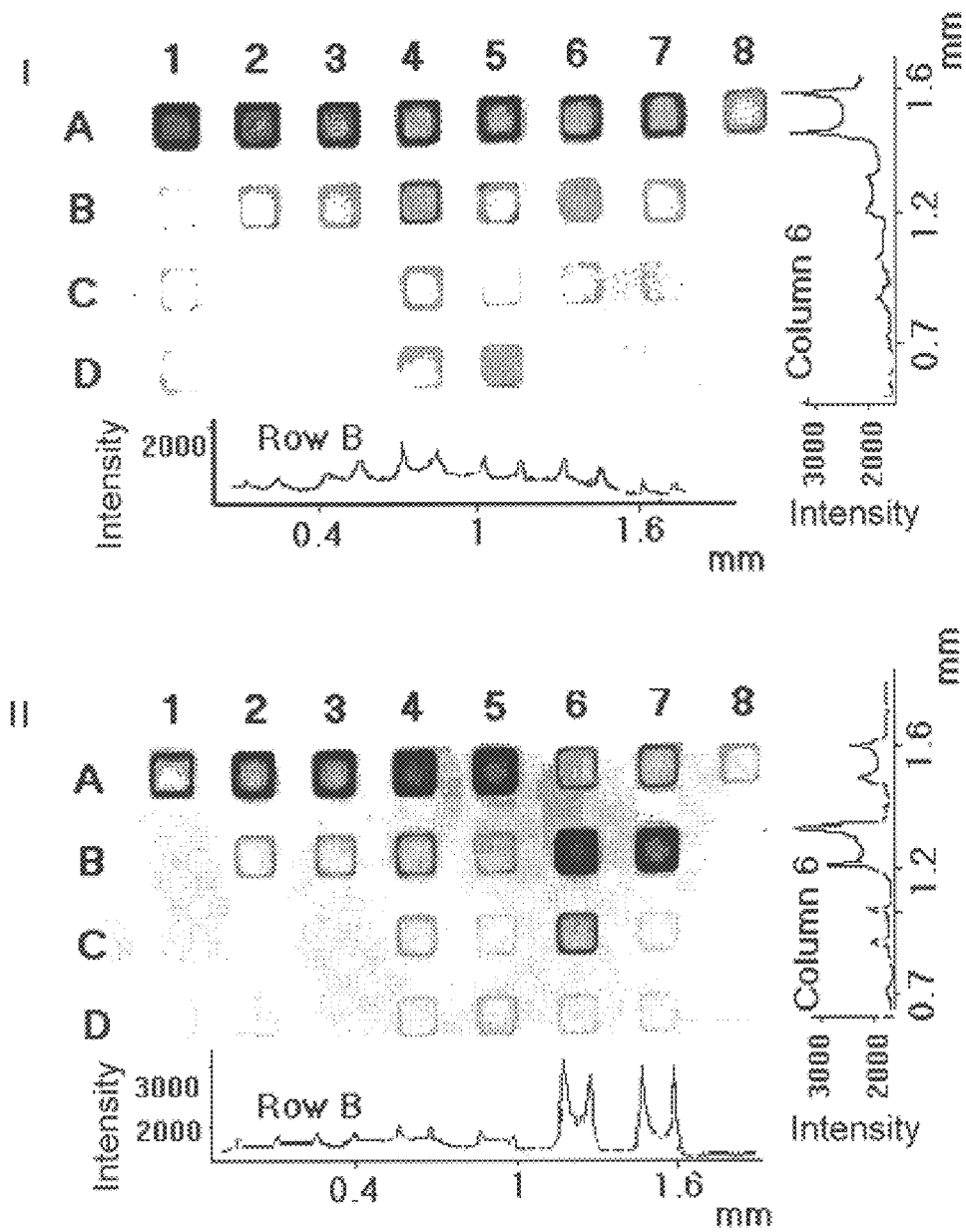
FIG. 9 shows reproductions of microchips used to identify rifampin-resistant mutations in *M. tuberculosis* genomic DNA isolated from a clinical specimen (sputum); the identification is performed by allele-specific PCR amplification.

Some signals for amplification of the wild type primer with mutated DNA curve 1 in FIG. 8 probably corresponded to the substantially weaker hybridization of the amplified product with the unextended or slightly extended primers. Upon amplification, the duplexes formed with the unextended or slightly extended primers hybridized with the upper labeled strand were dissociated in 0.3 M NaCl at 80° C. However, the more stable duplexes formed by the hybridization of extended immobilized primers with the fluorescently labeled upper strand remained within gel pads and were quantitatively assessed. FIG. 9 shows identification by this method of the C→T 1367 mutation which (see Table 5) causes the Ser 531 to Leu substitution in the RNA polymerase β-subunit. The ratio of a wild and mutant DNA in a sample could be compared by quantitative scanning the corresponding gel pads (FIG. 9). The validity of this mutation identification was corroborated by direct sequencing. The procedure took about 1 hour to perform, and was sensitive enough to detect the mutations in about $10^2$ *M. tuberculosis* cells.

FIG. 9 illustrates identification of rifampin-resistant mutations in *M. tuberculosis* genomic DNA isolated from a clinical specimen (sputum) by allele-specific PCR amplification. The microchip contained immobilized primers specific for wild bacterial strain (Row A) and different mutations (rows B-D) arranged in separate columns (1–8). The sequences of these immobilized primers, indicated by the numbers and letters corresponding to their arrangement in the proper columns and rows are shown in Table 5. Note that the gel pads 6A and 7A as well as 6B and 7B contained identical immobilized primers. The mutations were identified by comparing fluorescence intensities of the immobilized primers for wild type (6A, 7A) with mutated sequences (6B and 6B) after the microchip amplification with wild type (I) or mutant DNA (II). The microchip scans of row B and column 6 are shown below and to the right of the microchips, respectively.

Figure 10:
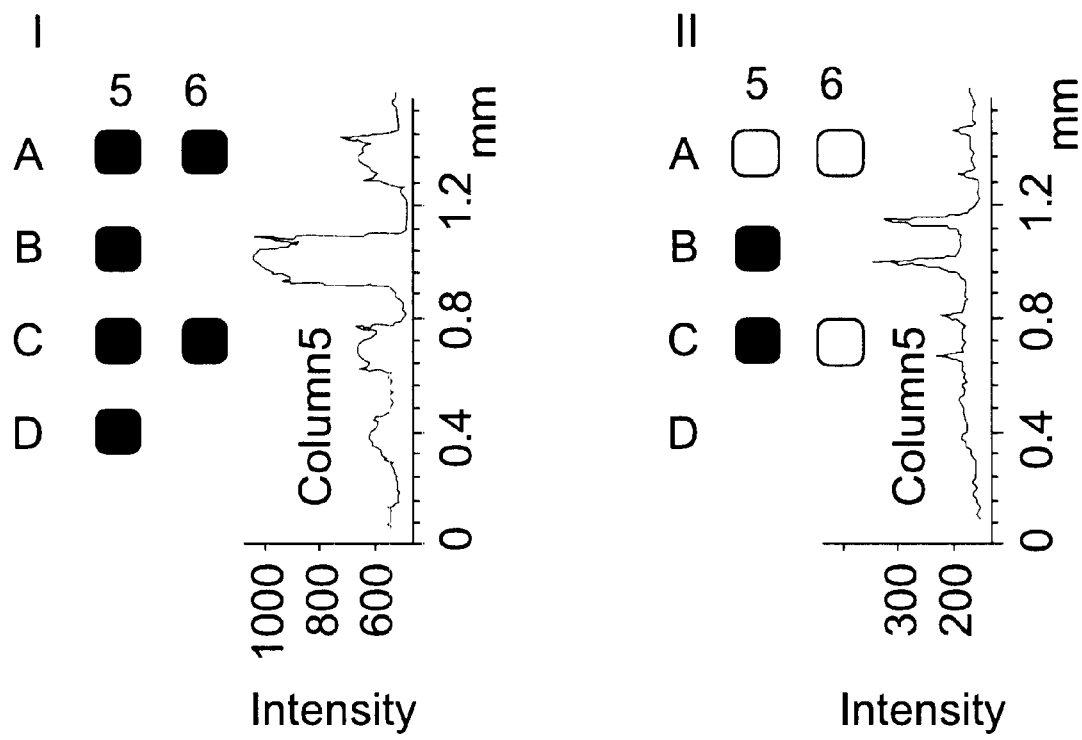
FIG. 10 compares microchips after PCR amplification on porous (I) and standard gels (II) with rpoB gene primers.

FIG. 10 shows the comparison of PCR amplification within standard polyacrylamide and porous gel pads with rpoB primers. Melting curves were monitored in real-time with the fluorescence microscope for both gel pads. Amplified fluorescently labeled duplexes fixed through immobilized extended primers were smoothly distributed within porous gels and located on the periphery of standard gel pads. The porous gels also demonstrated higher amplification signals. The same microchip used in FIG. 9II, and another one prepared by immobilization of the same primers on porous gel pads (I), were used in PCR amplification. The patient DNA contained A to G substitution at the 1352 position of the rpoB gene, which corresponded to His to Arg substitution in the protein. A significant increase occurred in the intensity of 5B pads for mutated DNA as compared with the 5A pad hybridized with wild-type DNA (see FIG. 9I).

TABLE 4

Primers Used For The Detection Of The Human BRCAL Gene

| Oligonucleotide | Positions* | Sequence 5' → 3' | $T_{an}$° C.** |
|---|---|---|---|
| brcal-F | 2639 | AAT GGA AGA AAG TGA ACT TGA TGC TC SEQ ID NO:38 | 58 |
| brcal-R | 2746 | CAT TCC TCT TCG CAT TTC CTG G SEQ ID NO:39 | 58 |
| brcal-P | 2673 | GCA GAA TAC ATT CAA GGT TT SEQ ID NO:40 | 59 |
| brcal-IP | 2714 | GGA GCA AAT GAC TGG CGC T SEQ ID NO:41 | 59 |
| brcal-IP2 | 2688 | GGT TTC AAA GCG CCA GTC ATT TGC TCC SEQ ID NO:42 | 65 |
| brcal-F,rib | 2639 | C6-C18-rUrU-C18-AAT GGA AGA AAG TGA SEQ ID NO:43 ACT TGA TGC TC | 58 |

*The column indicates the nucleotide position number, counting from the 5'-terminus of the gene encoding sequence.
**Annealing temperature, $T_{an}$ = $T_m$4 to 6° C. Melting temperature were calculated with Williamstone Software by the nearest neighbor method.

Example 6
PCR Amplification of Human Genomic DNA Within a Microchip Gel Pad Under Oil Amplification over (outside of) the microchip in the hybridization chamber takes place mainly in solution and only part of the reaction occurs within the gel pads. To carry out amplification only within the gel pads containing an immobilized primer, the microchip is covered with the amplification solution lacking this primer. All the components of the solution, including the second primer, DNA, and DNA polymerase are allowed to diffuse into the gel pads. The solution is then removed and the microchip is covered with oil. The oil prevents the exchange of solution, DNA, and primers between different gel pads. This allows PCR amplification to be performed within each gel pad without interference from other gel pads. Therefore, each gel pad behaves like a micro test tube. The scheme of the amplification under the oil is described in FIGS. 1C and D.

Forward terminal brcal-F and internal brcal-FI primers for the human brcal gene were immobilized within different microchip gel pads. About $4 \times 10^5$ molecules of human genomic DNA fragmented into pieces about 50–300 bp long were hybridized with the immobilized primers. The microchip pads were equilibrated with amplification solution and all its components diffused into the gel, including the fluorescently labeled reverse primer brcal-R. The solution was removed, the microchip was covered with oil, and PCR amplification was carried out for 40 cycles. After amplification, the duplexes formed on the extended immobilized primers were washed off from the excess of labeled reverse primer to detect the amplification with the fluorescence microscope. The microchip duplexes were then denatured and the labeled amplified upper DNA strand was washed off. Finally, the microchip primers that extended during the PCR procedure were hybridized with the labeled reverse primer brcal-R or the internal oligonucleotides probe brcal-PI to form duplexes within gel pads. This allows the specificity of amplification to be determined.

FIG. 21 shows the melting curves of microchip duplexes measured in real-time with the fluorescence microscope. The sharpness of these melting curves and their location at the high temperature range (72° C.) indicates the high specificity of the microchip PCR amplification carried out under oil.

The forward terminal-F and internal brcal-FI primers of the human brca1 gene were immobilized within different gel pads of a microchip (see FIGS. 1C and D) and were used in PCR amplification of fragmented genomic DNA under oil in the presence of reverse brcal-R primer diffused into the gel; the microchip immobilized primers brcal-F and brcalFI extended in PCR reaction were hybridized with Texas Red labeled internal probe brcal-PI (A) or reverse primer brcal-R (B) as shown in scheme in FIGS. 1E and F; the melting curves of the duplexes were measured with the fluorescence microscope.

FIG. 21 shows that the melting curves were very similar for duplexes formed by hybridization of the internal probe brcal-PI with the extended forward terminal brcal-F primer, or the internal brcal-FI primer. On the other hand, in FIG. 21, the level of hybridization was lower for duplexes formed by hybridization of the labeled reverse brcal-R primer with extended forward primer brcal-F as compared with extended forward internal primer brcal-FI. This effect may be accounted for by the lower efficiency of extension of the forward terminal primer brcal-F to the longer, full-size DNA strand as compared to the shorter, extended strand for the forward internal primer brcal-FI. No quantitative assessment of the efficiency at each step of such PCR amplification has been performed. It appears that 40 cycles of amplification with either of these two primers immobilized within gel pads of the microchip allowed one to detect the brcal gene from among $4 \times 10^5$ molecules of human genomic DNA.

Example 7
Release and Inactivation of Immobilized Primer

Two ribouridine nucleotides were introduced into immobilized deoxyribooligonucleotides at the 3' terminal region. The phosphodiester bonds at these residues are susceptible to digestion with pancreatic ribonuclease, RNase A. The microchip chimeric oligonucleotides were hybridized with a complementary fluorescently labeled probe and then digested with RNase A. The digestion released the gel immobilized $(dT)_{10}$ oligonucleotides into solution and exposed the 3' terminal phosphate group on the ribonucleotide residue of the remaining 3' dT-rU dinucleotide attached to the gel.

FIG. 22 shows cleavage and release of an immobilized chimeric oligodeoxyribonucleotide containing ribouridine nucleotides by ribonuclease A; the chimeric oligonucleotide 3' dT-(rU)$_2$-(dT)$_{10}$$^{-5'}$ was immobilized within a gel pad of a microchip and hybridized with fluorescently labeled complementary 10-mer 3' TMR-(dA)$_{10}$$^{-0.5'}$ The kinetics of cleavage of the immobilized chimeric oligonucleotide with ribonuclease A and the disappearance of the fluorescently labeled duplex from the gel pad was monitored in real time with the fluorescence microscope. The complete cleavage of the immobilized primer and the ensuing disappearance of the labeled probe hybridized to it occurred within 5 min. In addition, the presence of 3' terminal phosphate group in the dinucleotide remaining attached to the gel inactivates it for any polymerase reaction. The development of primer release for the real PCR connected process on microchip under oil was done in the following experiments (see FIGS. 14–19 ). It was found that 5'-ribo-region-rUrUrC-(in immobilized on chip oligonucleotide) is a much better substrate than rU-rU for digestion with Rnase A. An addition of Rnase A at a concentration of 200 ug/ml and BSA at a concentration 1 mg/ml were found optimal for both RNase A treatment and PCR amplification on chip under oil.

Example 8

Activation of Gel Immobilized Primer

The presence of a phosphate group at the 3' terminal position of oligonucleotides precludes extension with a DNA polymerase. However, the oligonucleotides can be easily activated by removal of the phosphate group with a phosphatase. FIG. 20 illustrates activation of immobilized primers for DNA polymerase reaction by dephosphorylation of the 3' phosphate group; a 20-mer primer VI (see brcal-P, Table 4) containing a phosphate group (top row) or a free hydroxy group (bottom row) at the 3' terminal position were immobilized within the microchip gel pads; the primers were hybridized with a complementary ssDNA (107 bases in length); the microchip was used in the single base extension reaction with DNA polymerase in the presence of four fluorescently labeled dideoxynucleoside triphosphates such as (A) and after on-chip dephosphorylation with alkaline phosphatase (B). FIG. 20 shows such an activation. Two rows of microchip gel pads contained either 3' terminally phosphorylated (top row) or nonphosphorylated (bottom row) immobilized primer VI. The microchip was hybridized with complementary single strand (ssDNA) and DNA polymerase single base extension of the microchip-immobilized primers was performed with a mixture of fluorescently labeled dideoxyribonucleotide triphosphates. PCR was carried out on the microchip as described by Dubiley et al. (1999). Only the non-phosphorylated primers were extended and fluorescently labeled under these conditions (FIG. 20A). After treating the microchip with alkaline phosphatase, the phosphate blocking groups were removed from the activatable primers, freeing the OH terminal group of the activatable immobilized primer making it available for DNA polymerase reaction. The repeated single base extension procedure was repeated, and a fluorescently labeled base was incorporated in the immobilized primers activated by dephosphorylation (FIG. 20B). Similar experiments were performed using a product of the *M. tuberculosis* rpoB gene (FIG. 16).

Example 9

Release and Activation of Immobilized Primers Under Mineral Oil

Figure 11:
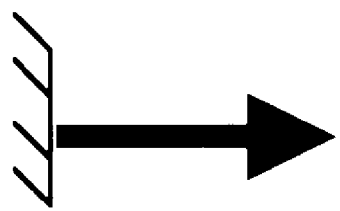
FIG. 11 shows symbols of primers to be immobilized on microchip gel pads;
(1) P-Standard primer (permanently immobilized could be used for enzymatic reactions);
(2) P$^r$-detachable temporary immobilized primer (could be released from the gel pads);
(3) P$^i$-Activated temporary inactive primer (could be activated); and
(4) P$^a$-Inactivated temporary active primer (could be inactivated).
Figure 11:
Figure 11:
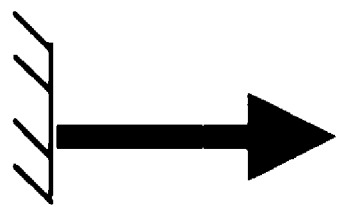
Figure 11:
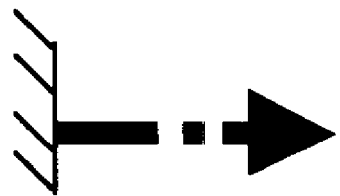
Figure 12:
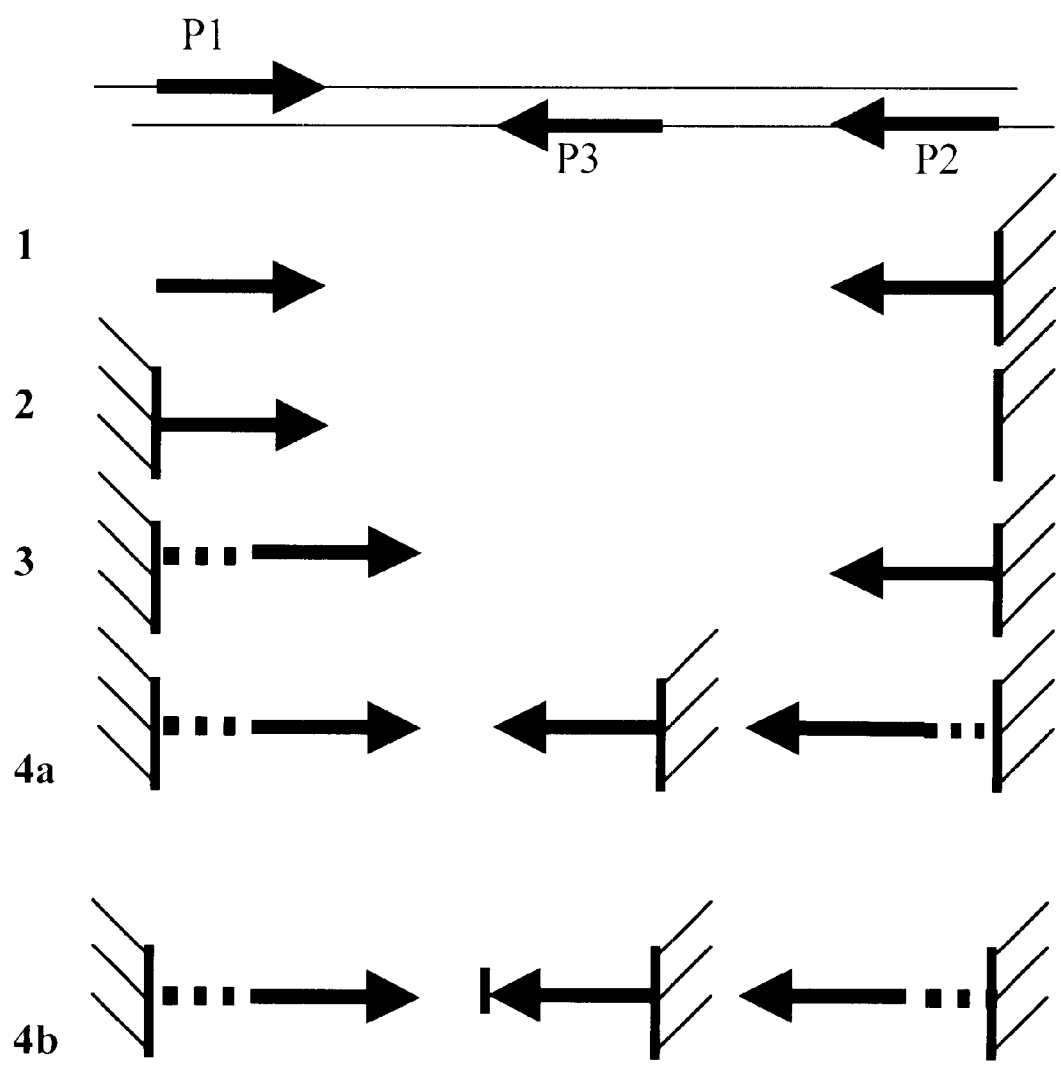
FIG. 12 illustrates different cases of primer immobilization in one gel pad to perform PCR amplification under oil; different types of primers P1, P2 (and P3) are as in FIG. 11.

The effectiveness of PCR under oil was successfully demonstrated in several situations using detachable, activatable, and inactivatable primers. Gel pads with specific sets of immobilized primers were separated from each other using mineral oil. Mineral oil interacts with hydrophobic glass surface between gel pads and covers hydrophilic gel to isolate the covered gel pads like test tubes. The variable 81 base-pair region of *Mycobacterium tuberculosis* rpoB gene (codons 507 through 533) was used as a model system. Mutations in this region are associated with rifampicin resistance, making the region important for tuberculosis therapy. FIG. 11 and FIG. 12 show the scheme of different sets of primers used. FIG. 11 shows the definitions of primers to be immobilized on microchip gel pads.

FIG. 12 shows different cases of primer immobilization in one gel pad to perform PCR amplification under oil. 1. One primer is a standard immobilized primer and one primer is a free primer coming from preincubation solution. 2. Both primers are standard immobilized primers. 3. One of two immobilized primers is standard and another one is detachable (temporary immobilized) primer. 4. Set of primers to perform a combinatorial PCR analysis. The simple example is shown as a set of three primers, two of which are detachable primers while the third one is a standard or activated temporary inactive primer.

TABLE 6

Primers Used For Combinatorial Analysis of M.tuberculosis Rifampicin Resistant Mutations

| No. | Name (*) | 5' end position | Sequence 5' → 3' (*) | T(an) °C. () | Comment (wild type-wt, mutant-mt) |
|---|---|---|---|---|---|
| 1 | Pr1 | 2333 | GGT-CGC-CGC-GAT-CAA-GGA-GT SEQ ID NO:44 | 67 | Direct, wt |
| 2 | Pr2 | 2469 | CGG-CAC-GCT-CAC-GTG-ACA-GA SEQ ID NO:45 | 67 | Reverse, wt |
| 3 | 1326 | 2352 | ACT-CCT-TGA-TCG-CGG-CGA-CC SEQ ID NO:46 | 67 | Reverse, wt |
| 4 | 1423 | 2432 | CGA-CAG-TCG-GCG-CTT-GTG SEQ ID NO:47 | 62 | Reverse, wt |
| 5 | 1424 | 2432 | CGA-CAG-TCG-GCG-CTT-GTA SEQ ID NO:48 | 61 | Reverse, mt (46302) |
| 6 | 1425 | 2381 | CAT-GGA-CCA-GAA-CAA-CCC-GCT-GTC-G SEQ ID NO:49 | 73 | Direct, wt |
| 7 | 1586 | 2387 | CCA-GAA-CAA-CCC-GCT-GTC SEQ ID NO:50 | 57 | Direct, wt |
| 8 | 1587 | 2387 | CCA-GAA-CAA-CCC-GCT-GTT SEQ ID NO:51 | 57 | Direct, mt (42151) |
| 9 | 1588 | 2398 | CGC-TGT-CGA-GGT-TGA-CCC SEQ ID NO:52 | (~56) | Direct wt |
| 10 | 1589 | 2398 | CGC-TGT-CGA-GGT-TGA-CCT SEQ ID NO:53 | (~54) | Direct mt (46302) |

TABLE 6-continued

Primers Used For Combinatorial Analysis of M.tuberculosis
Rifampicin Resistant Mutations

| Name No.(*) | 5'end position | Sequence 5' → 3'(*) | T(an) °C.() | Comment (wild type-wt, mutant-mt) |
|---|---|---|---|---|
| 11 | 1590 2399 | GCT-GTC-GAG-GTT-GAC-CCA SEQ ID NO:54 | (~54) | Direct, wt |
| 12 | 1591 2399 | GCT-GTC-GAG-GTT-GAC-CCT SEQ ID NO:55 | (~53) | Direct, mt (1811) |
| 13 | 1592 2414 | CCA-TAA-GCG-CCG-ACT-GTC SEQ ID NO:56 | (~56) | Direct, wt |
| 14 | 1593 2414 | CCA-TAA-GCG-CCG-ACT-GTG SEQ ID NO:57 | (~56) | Direct, mt (863) |
| 15 | 273A 2477 | CTC-CAG-CCC-GGC-ACG-CTC-ACG-T SEQ ID NO:58 | 73 | Reverse, wt |

*Primer modifications: 1325 = 5'-NH$_2$-Pr1-3'; TxR-1325 = 5'-Texas Red-Pr1-3'; 1326 = 5'-Texas Red - (20-mer)-3'; 1261 = 5'-NH$_2$- rUrU-Pr1-3'; 1333 = 1530 = 5'-NH$_2$-rUrUrC-Pr1-3'; 1334 = 5'-NH$_2$-rUrUrC-Pr1-FITC-3'; 1262 = 5'-NH$_2$-Pr2-3'; 1339 = 1531 = 5'-NH$_2$-rUrUrC-Pr2-3'; 1423 = 1424 = 5'-NH$_2$-(18-mer)-3'; 1425 = 5'-Texas Red-(25-mer)-3'; 273A = 5'-Texas Red-(22-mer)-3'; 1586 = 1587 = 1588 = 1589 = 5'-NH$_2$-(18-mer)-3'; 1590 = 1591 = 1592 = 1593 = 5'-NH$_2$-(18-mer)-3'-Phosphate (all above - 3'-OH).
**Annealing temperature, T$_{an}$ = T$_m$ (4 to 6)° C. Melting temperature was calculated with Williamstone Software. by the nearest neighbor method.

Common features of the 3 and 4 from FIG. 12 are primers released through RNase A digestion and the use of detachable primers for PCR under oil. Test experiments in test tubes and then on microchips were performed to define optimal conditions for both RNase A treatment and PCR amplification on microchips under oil:

1) RNase A concentration between 100–500 mkg/ml, where 200 mkg/ml was selected as a standard;
2) Bovine Serum Albumin (BSA) in concentration of 10–2000 mkg/ml was found to be very helpful to overcome an inhibition of PCR by RNase A in high concentration (the strongest effect was for BSA in concentration of 1000 mkg/ml);
3) The 5'-ribo-region -rU-rU-rC-(in immobilized on chip oligonucleotide) was found to be a better substrate than -rU-rU- for digestion with RNase A; and
4) Reversible RNase inactivation due to forming a complex with a specific inhibitor RNasin followed by (under mineral oil) transformation of RNase to active state by increasing the temperature (95° C.).

Figure 14:
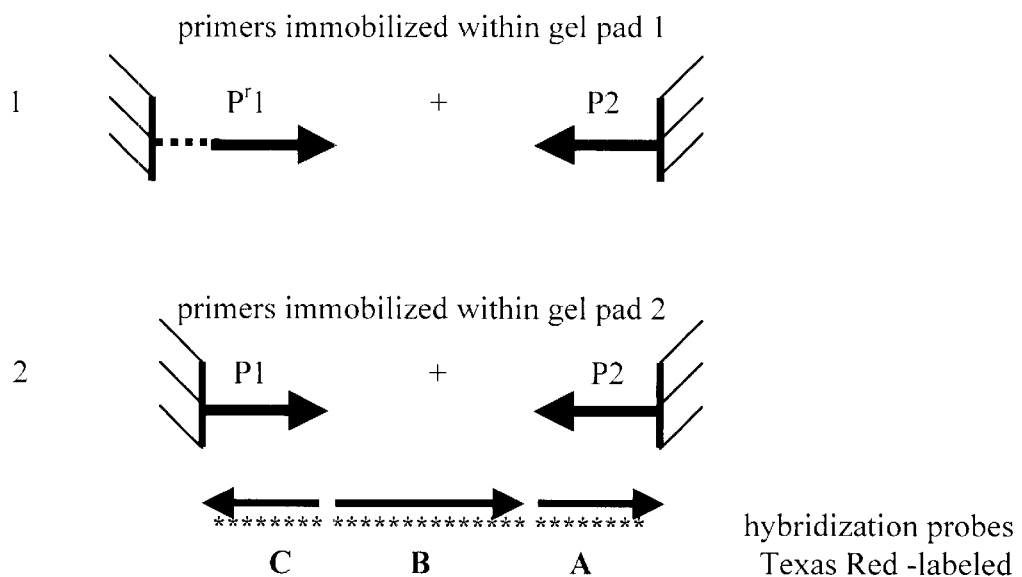
FIG. 14 shows (A) PCR detection analysis within gel pads with one primer P$^r$1 fated to be released and one standard primer P2 (1) or, with two standard primers P1 and P2 (2); (B) patterns of gel pads wherein;
(a) an initial pattern of gel pads with immobilized primers (hybridization of Texas Red—labeled probe with P2 primer).
Figure 14:
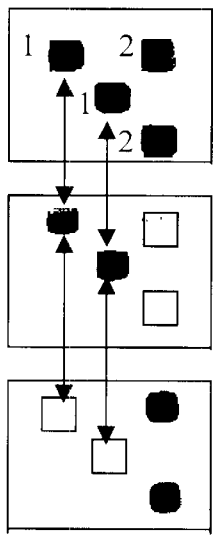

First, one of two initially immobilized primers was released by RNase A treatment prior to the initiation of PCR. Two ribouridine and one ribocytosine (-rU-rU-rC-) were introduced into the 5' region of one of the immobilized primers. The phosphodiester bonds at these residues are susceptible to digestion with pancreatic ribonuclease. Prior to PCR initiation, the detachable primer was released via RNase A digestion. RNase A had been included in the solution, as well as bovine serum albumin in concentration of 1000 mkg/ml and in some experiments RNasin, a RNase A inhibitor (optional). The BSA acted to neutralize the inhibitory effect of RNase A on PCR, while the RNasin prevented premature release of the primer into the solution during the initial incubation. Following incubation with solution, the solution was removed and the pads covered with oil. When the microchip was heated to 950° C., the RNasin ceased to inactivate the RNase A which digested the phosphodiester bonds of the ribonucleic oligonucleotides (at 37° C. for 30 min) and released the primer into the interior of the gel ad. Again, the individual primers in each of the pads would not migrate between pads because the pads were isolated by the hydrophobic oil. Using fragmented M. tuberculosis genomic DNA and approximately $10^5$ copies of amplicons, specific primer extension was demonstrated in gel pads where one of two primers was released after treatment with RNase A (FIG. 14). FIG. 14 illustrates PCR detection analysis within a gel pad with one primer P$^r$1 fated to be released with one standard primer P2 (1) or, within the gel pad, with two standard primers P1 and P2 (2). One immobilized primer (P2) is the same for both types of gel pads. Another primer (modification of P1) is different in its ability to be released after additional treatment (treatment with RNase A). Primer P$^r$1 (1) has a 5' ribonucleotide sequence rUrUrC which could be digested using RNase A. Primer P1 is released as result of the treatment. Hybridization was carried out in 0.5M NaCl with Texas Red labeled probes (a) an initial pattern of gel pads with immobilized primers (hybridization of Texas Red-labeled probe with P2 primer); (b) Detection and analysis of PCR product (hybridization with extended region of P2 primer); (c) detection of the primer P$^r$1 release during the experiment (hybridization with primer P1).

In another demonstration, (FIG. 12, case 4; FIG. 15), three primers were originally immobilized to the gel pad, one of which nested within the other two, i.e. were hybridized to a DNA sequence between the two extended genes. Again, about $10^5$ copies of fragmented M. tuberculosis were used as target DNA. The two outer primers contained a 5'-rU-rU-rC sequence, and were subsequently activated and released when treated with RNase A. Next, two stages of PCR under oil were performed, at two different annealing temperatures. For the first stage, the annealing temperature was selected to be higher than the annealing temperature of the inner, immobilized primer, but corresponding to the annealing temperature of the released primers. 35 PCR cycles were performed at this temperature.

The second PCR step was carried out after imer primer (P$^i$3) is activated. 3' blocking phosphate group was removed by alkaline phosphates as treatment. The annealing temperature was lowered to the ideal annealing temperature of the inner, immobilized primer. Several (3–10) cycles were performed with this lower annealing temperature. FIGS. 17, 18 and 19 show the hybridization signals from oligonucleotide sequences from the inner extended regions. Stronger signals correspond with "perfect match" primers, while weaker signals correspond to gel pads with 3' mismatched primers. Pads with two side (exterior) primers, only one of which was released, gave the faintest signals, corresponding to the least PCR product (FIG. 17).

Several variations on the aforementioned method can be derived to amplify a given specific sequence. These variations include: using additional PCR cycles with lower annealing temperatures; annealing at lower temperature then washing the microchip, replacing the buffer, and using a PCR enzyme with higher discrimination for primer extension, a single base extension reaction, or ligation reactions. FIG. 12 diagrams several of the variations of primer selection that can be made for one gel pad.

Figure 13:
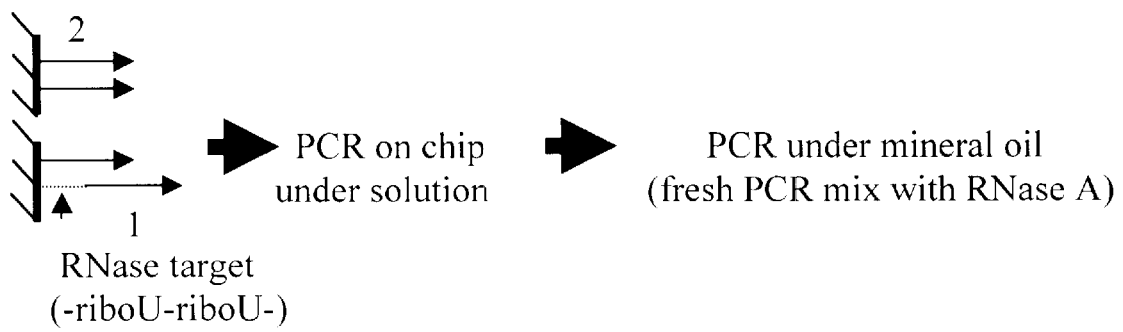
FIG. 13 (A) shows the design of an experiment wherein the 136 bp variable region of the *M. tuberculosis* RpoB gene was used as a model for PCR amplification on gel pads with two immobilized primers; (B) shows melting curves 1=partial release of the primer 2=no release.
Figure 13:
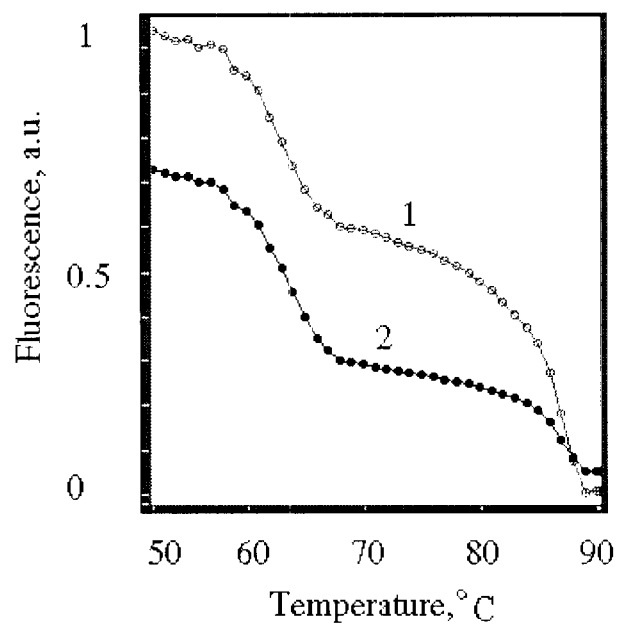

FIG. 13 illustrates that the 136 bp variable region of *M. tuberculosis* spo B gene was used as a model for PCR amplification on gel pads with two immobilized primers. (A) The scheme of the experiment is shown at the top. This is a demonstration of the PCR efficiency improvement when one of the two standard immobilized primers is replaced with a detachable primer. Unfortunately, RNase A treatment was ineffective. Less than 10% of primer with rUrU region at the 5' end was released according to hybridization data. (B) The figure at the bottom shows an example of melting curves of hybrids formed between extended immobilized (standard, in both cases) primer and a Texas Red labeled 136nt single strand DNA probe of the same region. The pattern (most of the hybrids are stable at temperatures above 80° C.) reflects the synthesis of expected long PCR product. Partial release of the primer in case 1 (detachable primer has 5' ribonucleotide region) seems to improve the final PCR result (compare curves 2 and 1). PCR in both cases is dependent on target DNA concentration (it was demonstrated for $10^7$ copies of amplicon and was not successful for $10^4$ copies of bacterial DNA with a 2hr hybridization step) and it needs both primers. Standard PCR solution (67 mM Tris-HCl, pH 8.6, 2.5 mM $MgC_2$, 16.6 mM $(NH_4)_2SO_4$, 0.001% Triton X-100, 2.5 ug of Taq Polymerase in 30 mkl) was used and all primers were immobilized on chip.

FIG. 15 diagrammatically shows combinatorial PCR amplification within a gel pad with three immobilized primers. Two primers ($P^r1$, $P^r2$) are fated to be released and then used in the first PCR amplification step (Step 1). These two primers are going to be removed after the hybridization of PCR product to immobilized inner inactive primer $P^i3$ (Step 2). Primer $P^i3$ should be activated (Step 3) to carry out the second amplification (or extension) step (Step 4). Fluorescently labeled oligonucleotides or dNTPs are used to detect the extension of the P3 primer.

FIG. 16 shows activation of modulated temporary inactive immobilized primer $P^i3$ single base extension (SBE) on chip: a) SBE without mineral oil using amplicon DNA without amplification of chip (A, B); or b) SBE after PCR amplification within gel pads under oil using the fragmented genomic DNA as a sample DNA (C, D). A set of three immobilized primers (as for a combinatorial PCR, FIG. 15) was used. Arrows indicate locations of gel pads with inner, temporary inactive primer $P^i$. $P^1$ has the phosphate group at its 3' end, the blocking group. Treatment with alkaline phosphatase removes this group and activates the primer for the following extension reaction. Similar results were obtained using porous gel pads (C, D) or standard gel pads with a hole inside (A,B).

FIG. 17 shows combinatorial PCR/mutation detection analysis within gel pads with three immobilized primers. Two primers ($P^r1$, $P^r2$) were released and used during the first PCR step. These two primers were then removed after the hybridization of PCR product to the immobilized inner primer $P^i3$ (P3a—"perfect match" primer [1423] and P3b—"3' mismatch" primer [1424] for the used DNA sample). The second PCR step was carried out after $P^i3$ is activated. Texas Red-labeled oligonucleotide probe (1425-TxR) was used to detect extended region of primer P3. About $10^5$ copies of fragmented wild type *M.tuberculosis* DNA were taken for the initial hybridization on a chip.

FIG. 18 shows combinatorial PCR on chip under oil used for mutation detection. A set of three immobilized primers was used. Two primers (side exterior primers, specific region PCR amplification primers) were released under oil through RNase A treatment. The third (inner) immobilized primer was used for mutation detection at the end of PCR amplification. Three cycles of primer extension were used (A and B). Additional phosphatase treatment was added before final extension in the case where immobilized primers with 3' phosphate blocking groups were used (B). About $10^5$ copies of fragmented DNA were taken. Numbers 863, 42151—are names of known point mutations (mt) and numbers 1587, 1593—are inner immobilized primers carrying corresponding changes at their 3' ends. Numbers 1586 and 1592 are inner primers corresponding to wild type DNA. Common released side primers ($P^r1$ and $P^r2$) were used in all cases.

FIG. 19 PCR on chip under oil was performed for synchronous analysis of three genetic regions using independently working gel pads of the same microchip. I—DNA sample carrying known mutations in rpoB gene (Ser522Leu) and in katG gene (Ser315Thr). II—DNA sample carrying known mutation in rpoB gene (Ser531Trp). Both samples do not have the mutation sought in rpsL gene. One chip was used for the analysis of each sample of I and II. FIG. 19 shows three sectors of the same chip for both cases. These sectors represent gel pads with primers designed for analysis of drug resistance related mutations in three different genes (columns from left to right; 4 positions in rpoB gene, 1 position in katG gene and 1 position in rpsL gene). All gel pads used for the analysis have sets of three gene specific, initially immobilized primers. Two primers are fated to be release under oil and used for the first PCR amplification step. The third inner, temporary inactivated primer is fated to be activated at the final step and used for mutation detection in the second round of PCR under oil (see FIG. 5). The upper row (from 3 rows) gel pads contain wild type inner primer. The bottom row gel pads contain specially designed inner primers carrying known mutation sequences, at a nucleotide substitution at their 3' end. FIG. 19 shows the final result of the combinatorial PCR analysis, and the hybridization signals corresponding to extended specific inner primers. From the comparison of the signals between gel pads carrying wild type and mutant inner primer, it can be determined if the sample DNA has a mutation in the corresponding position. Detected mutations (corresponding gel pads are marked by arrows) correlated with expected pattern.

The melting curves are very similar when internal probe brcal-P1 was used (A). The level of hybridization was lower for duplexes formed on gel pads with extended forward primer bracl-F that those formed on gel pads with extended forward inner primer brcal-F1 when labeled reverse primer bracl-R was used as a hybridization probe (B). This effect may be accounted for by the lower efficiency of extension of the forward terminal primer to the longer full-size DNA strand as compared to the shorter extended strand for the forward internal primer. It appears that 40 cycles of amplification with either of these two primers immobilized within gel pads of the microchip allowed one to detect the brac1 gene among 400,000 molecules of human genomic DNA.

FIG. 22 shows cleavage and release of an immobilized chimeric oligodeoxyribonucleotide containing ribouridine region, which is being digested by ribonuclease A. The chimeric oligonucleotide 3'-dT-(rU)2-(dT)10-5' was immobilized within a gel pad of a microchip and hybridized with fluorescently labeled complementary 10-mer 3' Texas Red-(dA)10-5'.

The kinetics of cleavage of the immobilized chimeric oligonucleotide with ribonuclease A and the disappearance of the fluorescently labeled duplex from the gel pad was monitored in real time with fluorescence microscope. The complete cleavage of the immobilized primer and the disappearance of the labeled probe occurred within 5 minutes. In addition, the presence of 3' terminal phosphate group in the dinucleotide remaining attached to the gel inactivates it for any polymerase reaction.

Material and Methods
Oligonucleotides, Amplicons and DNA

The variable regions of RNA polymerase β-subunit gene (rpoB) (2336–2472 bps, accession number L27989 of Gene Bank), of katG gene (2873–3002 bps, accession number X68081 of Gene Bank) and rps gene (83–192 bps, accession number X70995 of Gene Bank) were used for PCR amplification under oil.

The primers for PCR amplification were synthesized on a 394 DNA/RNA synthesizer (Applied Biosystems, Foster City, Calif.), using standard phosphoramidite chemistry. Both primers that were immobilized within microchip gel pads and those that were fluorescently labeling contained, at the 5'-terminal position, an amino link with a $C_6$ spacer (Glen Research, Sterling, Va.). Texas Reds® (5-carboxytetramethylrhodamine succinimidyl ether) (TMR, Molecular Probes Inc., Eugene, Oreg.) was linked to the 5' terminal amino groups of the oligonucleotides according to the manufacturer's protocol.

Chimeric oligonucleotides containing both deoxyribo- and ribonucleotide residues were deprotected by ammonia followed by treatment with 1 M tetrabutylammonium fluoride. Oligonucleotides were purified by reverse-phase HPLC.

Two B. anthracis amplicons of the lef gene encoding the lethal factor, and the pag4 gene encoding the protective antigen, were obtained from the U.S. Army Medical Research Institute of Infectious Diseases (USAMRIID). The 103 bp lef fragment (nucleotides/position nos. 1153–1255 of accession number M30210 of GenBank) and the 248 bp pag4 fragments (nucleotides position nos. 1931–2178 of accession number m22589 of GenBank) were generated by PCR amplification of the B. anthracis amplicons.

Plasmid pUC18 (Sigma Chemical Co., St Louis, Mo.) containing an ampicillin resistance (bla) gene was used for PCR amplification of the 2656–2748 base fragment of the gene (accession number AF074376 sequence of GenBank).

Plasmid pSHT23 containing the Shiga toxin gene (sht) was used for PCR amplification of the 1619–1757-bp fragment (positions 127–265, GenBank accession number: AJ132761).

For Example 7, DNA from different strains of M. tuberculosis was isolated from clinical samples of sputum provided by Moscow Scientific and Clinical Antituberculosis Center. A freshly prepared 0.5% solution of N-acetyl-L-cysteine (NALC) in 2% NaOH was mixed with an equal volume of sputum and incubated for 40 min. at room temperature. Five volumes of 0.1 M Na-phosphate buffer, pH 6.8, were added to the mixture, followed by centrifugation for min at 3000 rpm in an Eppendorf centrifuge. The cell pellet was suspended twice in 1.5 ml of 10 mM TrisHCl, pH 8.0, containing 1 mM EDTA and centrifuged. The cells in the pellet were lysed in 50 µl of 1% Triton X-100, 1 mM EDTA, 10 mM TrisHCl, pH 8.0, at 95° C. for 15 min followed by centrifugation at 10,000 rpm in an Eppendorf centrifuge. DNA from the supernatant was used directly for PCR amplification of the 2339–2461-bp fragment of RNA polymerase µ-submit gene (rpo B) (GenBank accession number: L27989).

For Example 9, the clinical samples of M. tuberculosis were obtained from the Moscow Scientific Practical Center of the Struggle with Tuberculosis. A PCR amplified fragment of the brcal gene (Holt and Jensen, 1996) containing nucleotides nos. 2580–2746 (accession number AF005068 of GenBank) was prepared by amplification of 50 ng of human genomic DNA in the GeneAmp PCR System 2400 (Perkin Elmer) under the following conditions: 50 sec. at 58° C., 30 sec. at 72° C., 40 sec. at 94° C., for 35 cycles with brcalF and brcal-R primers (20 pMol each) in 100 µl of PCR buffer containing 2.5 mM $MgCl_2$, 10 mM KCl, 10 mM Tris-HCl, pH 8.3, 200 µM, each of dNTP, 5 U of Stoffel Fragment (Perkin Elmer).

A ss-DNA fragment of the human brcal gene (nucleotide nos. 2580B2746) was obtained by asymmetric PCR by using 10–50 fmol of ds DNA fragment and 30 pmol of primer brcal-R. The ss-DNA was purified and concentrated 10-fold on Microcon microconcentrator columns, model 30 (product N 42410, Amicon, Inc., USA). The oligonucleotide primers and probes used for PCR amplification and hybridization are described herein.

Oligonucleotide Microchips

A microchip for PCR amplification contained approximately 1–2 pmol of oligonucleotide primers immobilized through their 5'-terminal amino groups in 100×100×20-µm polyacrylamide gel pads or 100×100×40 µm porous mixed polyacrylamide gel pads spaced by a 200-µm hydrophobic glass surface. Two kinds of gels of different porosity containing active aldehyde groups were used for the microchip manufacturing.

Standard Acrylamide Gels

The polymerization solution contained 4.75% acrylamide (Sigma), 0.25% N,'-methylene bisacrylamide, 0.5% N-(2,2-dimethoxy)ethylene acrylamide (to introduce aldehyde groups into the gel), 0.1 M sodium phosphate, pH 7.0, 40% glycerol, 0.004% methylene blue, and 1.2% TEMED. The polymerization solution (100 µl) was vortexed for 3 sec., degassed for 3 min. with a water vacuum pump, and applied to the polymerization chamber. The chamber consisted of a glass microscope slide (Corning Glass Works, Corning, N.Y.) and a quartz chromium mask separated by two 20 µl Teflon® spaces. The gel was photopolymerized by illumination of the chamber with UV light in a Stratalinker UV oven at a distance of 4.5 cm from the lamp for 15 min. at room temperature.

The gel was activated with 2% trifluoroacetic acid at room temperature for 10 min to convert dimethoxy groups into aldehyde groups, washed with water and dried. Then the gel was consecutively treated with Repel-Silane (dimethyldichlorosilane solution 2% (w/v) in 1,1,1-trichloromethane, LKB-Produkter AB, Bromma, Sweden) for 30 sec., dichloromethane for 10 sec., and ethyl alcohol 95 vol. % for 10 sec. washed with water for 3 min., and dried (dichloromethane is optional).

One nanoliter of a 1 mM solution of the oligonucleotide containing the 5'-terminal amino group was applied by a pin robot onto the corresponding activated microchip gel pad containing the aldehyde group. The imino bonds formed between the 5'-amino groups of the oligonucleotide and the aldehyde groups of the gel pads were stabilized by reduction with pyridine-borane complex (Aldrich Chemical Co., Inc., Milwaukee, Wis.). The reduction was performed by placing the micromatrix under 50 ml of a 0.1 M solution of pyridine-borane complex in water-saturated chloroform covered with 50 ml of water and incubated at room temperature overnight. The micromatrix was washed twice with ethyl alcohol and twice with water. The unreacted aldehyde groups of the gel were reduced with a freshly prepared solution of 0.1 M NaBH$_4$ (Aldrch) in water for 20 min. at room temperature. Finally, the oligonucleotide microchip was washed with water, dried, and kept at room temperature for up to 12 months.

Porous Gels

The polymerization solution contained 1.5% acrylamide, 1.5% N-acryloyltris(hydroxymethyl)aminomethane (BioRad, Hercules, Calif.) 0.7% N,N'-(1, 2dihydroxyethylene)bisacrylamide (Sigma), 0.2% N,N'-diallyltartardiamide (BioRad), 0.1% N,N'-methylene bisacrylamide (Sigma), 0.1 M Na-phosphate, pH 7.0, 1.2% TEMED, and 30% glycerol. After vortexing for 2–3 secs. and degassing for 3 min, 1.2 µl of acetone was added and photopolymerization was carried out for 28 min.

In order to produce aldehyde groups, the gel was activated by incubation of the gel micromatrix in 0.1 M NaIO$_4$ for 30 min. at room temperature. The micromatrix was washed with water for 10 min. and dried. The application and immobilization of oligonucleotide was carried out as described above for the standard gel.

PCR Amplification of a Genomic DNA Fragment Within a Microchip Gel Pad

Human genomic DNA (5 µg; ~4×10$^5$ copies, Sigma) was depurinated in 50 βl of 80% formic acid at 20° C. for 3 min. DNA was precipitated with 500 µl of 2% LiClO$_4$ in acetone, washed with acetone and dried. Depurinated DNA was incubated in 50 µl of 10% piperidine (Aldrich) at 90° C. for 40 min to fragment it to pieces of 50–300 nucleotides in length, precipitated and washed with acetone and dried. The fragmented DNA was hybridized for 3 h at 50° C. with forward primers brcal-F and brcal-P (Table 1) immobilized within different porous gel pads of the microchip, in 20 µl of PCR buffer containing units of AmpliTaq DNA polymerase Stoffel Fragment (Perkin Elmer, Place) and 10–50 pmol/µl of the reverse primer brcal-R. After annealing, the DNA solution was replaced with the PCR solution containing 2.5 mM MgCl$_2$, mM KCl, 10 mM Tris-HCl, pH 8.3, 0.1% bovine serum albumin (Sigma), 200 µM each of dNTP, units of Stoffel Fragment, 10–50 pmol/µl of the reverse primer, and incubated for 10–15 min at 50° C. The PCR solution was replaced with mineral oil for PCR (Perkin Elmer). The chip was thermocycled 35–40 times under the following conditions: 50 sec at 58° C., 30 sec at 72° C., 40 sec at 94° C. The microchip was then washed with 2 ml of chloroform and 1 ml of 0.2B0.3 M NaCl. Denaturing the microchip duplexes was carried out at 90° C. in 0.20.3 M NaCl for 10 min, washing off the complementary strand was with 200–300 µl of 0.2B0.3 M NaCl and hybridization of the extended microchip primer with a labeled probe was carried out as described herein.

Release of the Microchip-immobilized Primer

The release of the microchip immobilized chimeric oligonucleotides 3' gel-NH$_2$-dT-(rU)$_2$-d(T)$_{10}$ into solution was carried out by splitting the phosphodiester bonds of the ribonucleotide residues with pancreatic ribonuclease. The immobilized oligonucleotides were hybridized with a solution of fluorescently labeled oligonucleotides 3' TMR-(dA)$_{10}^{-5'}$ in 0.1 M NaCl, 10 mM Na-phosphate, pH 7.0, and 1% Tween at 20 at 23° C. for 12 h and was incubated with a 0.1% solution of RNase A (Sigma) in the same buffer at the same temperature. The reaction of release of the labeled immobilized duplex from the gel pads was monitored in real time with the fluorescence microscope.

Activation of the Microchip-immobilized Primer

The same 20-mer primers, non-phosphorylated or 3' phosphorylated, were immobilized within two rows of the microchip acrylamide gel pads and were used before and after dephosphorylation in the single base extension assay (Dubiley et al., 1999). Thirty µl of the reaction mixture contained about 1 pM ssDNA, 3 µM solution of each fluorescein-conjugated dideoxynucleotide triphosphate (ddNTP-FL, NEL400–NEL403, NEN DuPont, City, St), and 10–15 units of ThermoSequenase (Amersham, City, St) in 1×. ThermoSequenase reaction buffer (Amersham). The microchip containing the reaction mixture in the hybridization chamber was incubated at 69° C. for 3 h. Upon completing of the reaction, the microchip was washed with 1 ml of 1 M NaCl to remove fluorescently labeled ddNTPs, rinsed with water and observed under the fluorescence microscope. The microchip was then treated with a solution consisting of 3 units of alkaline phosphatase (Amersham) in 20 µl of 2 mM MgCl$_2$, 20 mM Tris-HCl, pH 9.5, for 2 h at 37° C. The phosphatase was inactivated at 70° C. for 20 min and the single base extension reaction was carried out as described herein.

PCR Amplification Over (Outside of) and Within (Inside) Microchip Gel Pads

A microchip chamber for PCR amplification and hybridization was manufactured by placing a quartz cover glass (20×35×3 mm) over the microchip glass microscope slide. The quartz plate contained two 1-mm channels (holes) holding silicone tubes as ports. The glass and quartz plates were separated by a 60-µm polyethylene spacer containing a hole the size of the gel pad. The sandwich was fixed with a aluminum clamp at 90 ° C. for min. The chamber was filled with 30 µl of PCR buffer through one of the silicone tubes. The PCR buffer contained 2.5 mM MgCl$_2$, mM KCl, 10 mM Tris-HCl, pH 8.3, 0.1% bovine serum albumin (Sigma), 200 µM each of dNTP (Sigma), 5 units of AmpliTaq DNA polymerase, Stoffel Fragment (Perkin Elmer, Foster City, Calif.), 1–10 pmol each of the forward unlabeled and reverse labeled primers, and 10$^4$ copies of bacterial genomic or amplicon DNA. 100 ng of phage λ DNA (Sigma) was added to the PCR mixture when less than 10$^4$ copies (10 ng) of DNA were used for amplification. After preheating at 95° C. for 120 sec., 25–35 cycles of PCR amplification were carried out at 95° C. for 30 sec., at annealing temperature for 50–60 sec., and 72° C. for 40–50 sec. The calculated annealing temperatures ($T_{AN}$) for the primers are shown in the Tables herein. However, the temperature used was 5–6° C. lower, because the gel decreases the melting temperature of duplexes. The thermocycling was carried by placing the microchip chamber on a Peltier thermotable of a fluorescent microscope. The kinetics of amplification were monitored by measuring the fluorescent signal exceeding the background in parallel for all gel pads of the microchip.

The hybridization chamber was disassembled after amplification, and the microchip was washed first with 1 ul and then with 100 ul of water at 90° C. for 10 min. each time and dried in air. Alternatively, the microchip was washed with 300 ul of water at 95° C. for 10 minutes. The hybridization of the microchip-immobilization primer that had been extended during PCR amplification with 30 µl of the Texas Red-labeled complementary probe (1 pmol/µl) was carried out in PCR buffer at 55° C. for 0.5 hr. The melting curves of the duplexes formed were measured with a fluorescent microscope by increasing the temperature at the rate of 0.5° C. per min.

RNase-dependent Primer Release and PCR Amplification Under Oil (See Example 9)

*M. tuberculosis* genomic DNA was depurinated in 50 μl of 80% formic acid at 20° C. 15 for seconds. DNA was precipitated with 500 mkl of 2% LiClO$_4$ in acetone, washed with acetone and dried. Depurinated DNA was incubated in 50 μl of 10% piperidine (Aldrich) at 90° C. for 40 min. to fragment it to pieces of about 100–300 nucleotides in length, precipitated and washed with acetone and dried. The fragmented DNA (20 ng; 10$^5$ genomic copies) was hybridized in 20 μl of hybridization buffer (0.5M NaCl, 0.1 mM EDTA, 10 mM Tris-HCl, pH 8.0) at 55° C. for 2 hr with primers immobilized within different gel pads of the microchip. The microchip was washed with 0.15M NaCl at 55° C. (200 μl×30 times). Standard PCR solution (67 mM Tris-HCl, pH 8.6, 2.5 mM MgCl$_2$, 16.6 mM (NH$_4$)$_2$SO$_4$, 0.001% Triton X-100, 1 mg/ml BSA, 0.24 mM of each dATP, dCTP, dGTP and dTTP, 2.5U Taq DNA Polymerase per 30 μl) was used for the following stages. The microchip was washed once and then incubated with the PCR solution for 15 min at 55° C. and for 5 min at 72° C. The final incubation was 1 min at 95° C., 10 min at 54° C. to anneal PCR products to the inner immobilized primer (case 4, FIG. 12). Following washing with 0.15 M NaCl at 54° C., primer extension or single base extension reactions were used for final detection analysis. The microchip oil was washed off with a large volume of 0.15 M NaCl. The microchip duplexes were denatured at 94° C. in 0.15 M NaCl for 5 min. and washed with several changes of the same solution. The analysis of extended primers on chip was performed by hybridization with labeled single strand DNA probes.

The Activation of the Immobilized Primers on Microchip and Single Base Extension Assay (Examples 7 and 8)

The same unphosphorylated and 3-'phosphorylated 20-mer primers were immobilized within two rows of the microchip acrylamide gel pads and were used before and after dephosphorylation in a single base extension assay (Dubiley et al., 1999). 30 μl of reaction mixture contained about 1 pMol ss DNA, 3 μM solution of each fluorescein-conjugated dideoxynucleotide triphosphate (ddNTP-FL, NEL400-NEl403, NEN Du Pont), and 10–15U of ThermoSequenase (Amersham) in 1× ThermoSequenase reaction buffer (Amersham). The microchip with the reaction mixture in the hybridization chamber was incubated for 30 min. at each of the following temperatures: 55° C. and 61° C. (the temperatures are near T$_m$ of immobilized primers). Upon completing the reaction, the microchip was washed with 1 ml of 0.1 5M NaCl to remove fluorescently labeled ddNTPs, rinsed with water and observed under fluorescence microscope. The microchip was then treated with the solution of 3U of alkaline phosphatase (Amersham) in 20 μl of 2 mM MgCl$_2$, mM Tris-Cl, pH 9.5 for 1 hr at 37° C. Phosphatase was carefully washed off with 0.1 M NaCl, and a single base extension reaction was carried out as described herein. Each buffer change was made after preincubation of the chip in the new buffer.

A similar procedure of primer activation was performed on the microchip after PCR under oil. PCR-synthesized DNA was hybridized to inner primers (immobilized on chip) at 55° C. for 20 min. Following washing with 0.15M NaCl, phosphatase reaction was performed and then, after washing and buffer change, the single base extension reaction was carried out under oil (to keep DNA in corresponding gel pads) at temperatures near T$_m$ of immobilized primers. 1 mg/ml BSA was added to ThermoSequenase reaction buffer.

Monitoring PCR Amplification and Its Specificity

Amplification was directly monitored by measuring the incorporation of a fluorescently labeled primer into the microchip gel pads. After PCR amplification the microchip was washed as follows: PCR buffer is changed with 0.1 M NaCl; the chamber is incubated at 94iC for 10 min; saline solution is changed to water; this chip is air-dried.

The length of PCR amplified fragments was determined by electrophoresis in 2% agarose gel.

Fluorescence Measurements

All experiments were performed in real time on an automatic experimental setup (Fotin et al., 1998) consisting of a fluorescent microscope, a 512×512 CCD-camera (3×3 mm$^2$ field of view), a Peltier thermotable, a temperature controller, a motion controller with step-motors, and a computer equipped with a data acquisition board. Special Hybridization Experiment Software© package was designed for experimental control and data processing, which uses a LabVIEW virtual instrument interface and software (National Instruments, Austin, Tex.).

DOCUMENTS CITED

Arenkov P., Kukhtin A., Gemmell A., Chupeeva V., Voloschuk S., & Mirzabekov A. Protein microchips : Use for immunoassay and enzymatic reactions. (2000) *Anal. Biochem.* 278, 123–131.

Dubiley, S., Kirillov, E., Lysov, Y., Mirzabekov, A. Fractionation, phosphorylation, and ligation on oligonucleotide microchips to enhance sequencing by hybridization. (1997) *Nucl. Acids Res.* 25, 2259–2265.

Dubiley, S., Kirillov, E., Mirzabekov, A. Polymorphism analysis and gene detection by minisequencing on an array of gel-immobilized primers. (1999) *Nucl. Acids Res.* 27, e19.

Fotin, A., Drobyshev, A., Proudnikov, D., Perov, A., Mirzabekov, A. Parallel thermodynamic analysis of duplexes on oligodeoxyribonucleotide microchips. (1998) *Nucl. Acids Res.* 26, 1515–1521.

Holt, J., Thompson, M. E., Szabo, C., Robinson-Benion, C. Arteaga, C.L., King, M. C., Jensen, R. A. Growth retardation and tumor inhibition by BRACAI. (1996) *Nat. Genet.* 12(3): 298–302.

Kozlov, Y., Kabishev, A., Lukyanov, E., and Bayev A. (1988) Title *Gene,* 67, 213–221.

Proudnikov, D., Timofeev, E., Mirzabekov, A. Immobilization of DNA in polyacrylamide gel for the manufacture of DNA and DNA-oligonucleotide microchips. (1998) *Analyt. Biochem.* 259, 34–41.

Yershov, G., Barsky, V., Belgovskiy, A., Kirillov, E., Kreindlin, E., Ivanov, I., Parinov, S., Guschin, D., Drobishev, A., Dubiley, S. and Mirzabekov, A. DNA analysis and diagnostics on oligonucleotide microchips. (1996) *Proc. Natl. Acad. Sci. USA* 93, 4913–4918.

We claim:

1. A method for performing PCR amplification of a nucleic acid molecule and parallel hybridization wherein amplified products are also identified by hybridizing them on the microchip within gel pads surrounded by a hydrophobic liquid, and analyzing melting curve patterns said method comprising:

(a) providing a microchip with a plurality of immobilized and non-immobilized PCR primers for each gel pad;

(b) adding a hybridization solution and the nucleic acid molecule to be tested to the microchip;

(c) replacing the hybridization solution with the amplification solution;

(d) modulating at least one of said immobilized primers;

(e) replacing the amplification solution with a hydrophobic liquid, so that the hydrophobic liquid surrounds the gel pads;

(f) cycling the temperature to achieve PCR amplification within each gel pad;

(g) repeating steps (a) to (f) wherein the immobilized primers are activated, inactivated, or detached from the gel pads; and (h) identifying the amplification products by hybridization and melting curve analysis on the microchip.

2. The method of claim 1, wherein the hydrophobic liquid is a hydrocarbon.

3. The method of claim 1, wherein the gel pads are porous.

4. The method of claim 2, wherein the hydrocarbon is mineral oil.

5. The method of claim 1 wherein the hybridization solution contains printers.

6. The method of claim 1, wherein at least one of the immobilized primers is a detachable primer, said detachable primer having the ribonucleotide sequence at the said primer 5' terminus, and wherein said ribonucleotide sequence is a target for enzymatic digestion by the ribonuclease, and the amplification solution further comprises the ribonuclease which detaches said set of detachable primers from the gel matrix, said ribonuclease selected at each repetition of steps (a) to (f) to detach a different set of detachable immobilized primers from the gel pads.

7. The method of claim 1, wherein at least one of the immobilized primers is an activatable primer, said activatable primer having the blocking group at said primer's 3' terminus, and the amplification solution further comprises an enzyme which removes said blocking group from the set of activatable primers, said enzyme selected at each repetition of steps (a) to (f) to remove a different blocking group from different activatable primers.

8. The method of claim 1 wherein the immobilized primers are selected from the group consisting essentially of forward primers, reverse primers, interior (nested) forward primers, and interior (nested) reverse primers.

9. The method of claim 1, wherein the step of modulating the immobilized primer further comprises the steps of changing the hybridization temperature to correspond to an annealing temperature of at least one of the immobilized primers being modulated, wherein said annealing temperature does not equal the annealing temperature of other immobilized primers.

10. The method of claim 8, wherein the step of modulating the immobilized primer comprises activating the immobilized primers.

11. The method of claim 10, wherein the step of activating the immobilized primer further comprises the steps of detaching a blocking group from the immobilized primer.

12. The method of claim 11, wherein the blocking group is a phosphate attached to the 3' hydroxyl terminus of the immobilized primer.

13. The method of claim 12, wherein the step of detaching the blocking group further comprises the step of treating the immobilized primer with a phosphatase enzyme.

14. The method of claim 8, wherein the step of modulating the immobilized primer further comprises the step of inactivating the immobilized primer.

15. The method of claim 14, wherein the step of inactivating the immobilized primer further comprises the step of degrading a ribonucleotide sequence between the 5' and 3' terminals of the immobilized primer with a ribonuclease enzyme.

16. The method of claim 15, wherein the step of inactivating the immobilized primer further comprises the step of degrading a ribonucleotide sequence at the 3' terminal of the immobilized primer with a ribonuclease.

17. The method of claim 16, wherein the step of inactivating the immobilized primer further comprises the step of treating a cis-vicunal dioxy group(—CHOH-CHOH-) with sodium periodate ($NaIO_4$).

18. The method of claim 1, further comprising the step of performing a primer base extension reaction on the PCR products of the target nucleic acid sequence.

19. A method for performing sequential PCR amplification of a target nucleic acid sequence, wherein the amplification occurs both outside of and within a plurality of gel pads on a microchip, said method comprising:

(a) providing a microchip with immobilized primers for each gel pad;

(b) adding a solution comprising an amplification solution, primers and a target nucleic acid sequence to the microchip;

(c) modulating said immobilized primers;

(d) cycling temperature of the microchip to achieve amplification;

and (e) repeating steps (a)–(c) wherein the immobilized primers are selectively activated, inactivated or detached from the gel pads.

20. The method of claim 19, further comprising running a detection reaction using the hybrid between the immobilized primer and PCR product of the nucleic acid sequence to be tested and wherein additional PCR, primer extension, single base extension or ligase reactions are used.

21. A method for performing PCR amplifications on a microchip comprising (a) amplifying a nucleic acid in solution over the microchip; (b) amplifying a short fragment over and within the microchip gel pads on immobilized forward internal primers; (c) hybridizing the extended immobilized primers with the amplified fluorescently labeled complementary strand; (d) monitoring hybridization in real time with a fluorescent microscope, wherein the specificity of the reaction was tested by hybridization of the extended immobilized primers with a labeled reverse primer or internal probe.

22. A method for performing combinatorial PCR amplification within a gel pad using three immobilized primers, $P^r1$, $P^r2$ and $P^i3$ said method comprising;

(a) releasing $P^r1$ and $P^r2$ primers;

(b) performing a first PCR step to form a product;

(c) hybridizing the PCR product to immobilized inactive primer $P^i3$;

(d) activating an immobilized primer $P^i3$; and (e) analyzing the amplified sequence using activated primer $P^i3$ for primer extension or single base extension reactions.

23. The method of claim 22 wherein many different genes and their polymorphic bases are detected simultaneously on one microchip using different gel pads working independently.

24. The method of claim 22 where all primers are chosen to work at the same reaction conditions allowing to carry out simultaneous and separate PCR amplifications within all microchip gel pads.

25. A detachable temporary immobilized primer wherein the primer detaches from a gel matrix and wherein upon the detachments by chemical treatment the primer and remains inside of a gel pad.

26. An PCR primer immobilized in a gel pad in a microchip comprising a ribonucleotide sequence at the 5' terminus of said primer, wherein said ribonucleotide is a target for enzymatic digestion by a ribonuclease, and wherein said primer is further designated as a detachable primer.

27. An PCR primer immobilized in a gel pad in a microchip, wherein the primer is bound to a blocking group which prevents the immobilized primer from participating in the PCR, and wherein said immobilized primer is further designated as an activatable primer.

28. A primer immobilized in a gel pad, wherein the immobilized primer contains at least one target for chemical digestion between the 5' and 3' terminals of the immobilized primer, and wherein said primer is further designated as an inactivatable primer.

* * * * *

UNITED STATES PATENT AND TRADEMARK OFFICE
CERTIFICATE OF CORRECTION

PATENT NO. : 6,642,000 B1
DATED : November 4, 2003
INVENTOR(S) : Strizhkov et al.

It is certified that error appears in the above-identified patent and that said Letters Patent is hereby corrected as shown below:

Column 51,
Line 65, please replace "the microchip" with -- a microchip --

Column 53,
Line 16, please replace "printers" with -- primers --

Column 55,
Lines 1 and 7, please replace "An PCR" with -- A polymerase chain reaction --

Signed and Sealed this

Twenty-ninth Day of June, 2004

JON W. DUDAS
*Acting Director of the United States Patent and Trademark Office*

SEQUENCE LISTING

<160> NUMBER OF SEQ ID NOS: 58

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
cccttgataa tatcttacc                                                    19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
gatatgaacc cgtacttg                                                     18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
caagttccca ggggttacta gg                                                22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
cacttcttgg tcatctaccc ac                                                22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
ttgttacatg attatcagcg gaa                                               23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
ccgcctccat ccagtctatt                                                   20

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 7
ctgtagcaat ggcaacaacg                                              20

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 8
tgccgggaag ctagagtaag tagttc                                       26

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
ttctttgtta tcttttcagt taatgtggtt                                   30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
ttctttgtta tcttttcagt taatgtggtg                                   30

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 11
ttctttgtta tcttttcagt taatgtggt                                    29

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
tacctcctga tgaaatagtc tgtaatgg                                     28

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 13
```
cgcgatcaag gagttcttcg gcacc                                          25

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 14
cccggcggtc tgtacgtga                                                 19

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 15
gcaccagcca gctgagacaa ttcatggac                                      29

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 16
gcaccagcca gctgagacaa ttcatggt                                       28

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 17
gcaccagcca gctgagccaa ttcatgt                                        27

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 18
gcaccagcca gctgagacaa ttcatggag                                      29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 19
gagccaattc atggaccaga acaacccgc                                      29

<210> SEQ ID NO 20
<211> LENGTH: 31
<212> TYPE: DNA
<213> ORGANISM: Artificial Sequence

```
<220> FEATURE:
<223> OTHER INFORMATION: Description of Artificial Sequence: Primer

<400> SEQUENCE: 20
ctgagccaat tcatggacca gaacaacccg a                              31

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 21
gccaattcat ggaccagaac aacccgctgt c                              31

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 22
gccaattcat ggaccagaac aacccgctgt t                              31

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 23
ccagaactac ccgctgtcgt ggttgaccc                                 29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 24
ccagaactac ccgctgtcgt ggttgacct                                 29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 25
ccagaactac ccgctgtcgt ggttgaccg                                 29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 26
ccagaactac ccgctgtcgt ggttgacca                                 29
```

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 27
agaactaccc gctgtcgtgg ttgaccca                              28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 28
agaactaccc gctgtcgtgg ttgacccg                              28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 29
agaactaccc gctgtcgtgg ttgaccct                              28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 30
agaactaccc gctgtcgtgg ttgacccc                              28

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 31
ggttgaccca caagcgccga ctgtc                                 25

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 32
ggttgaccca caagcgccga ctgttr                                26

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Primer

```
<400> SEQUENCE: 33
gggttgacca acaagcgccg actgtgt                                    27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 34
gggttgacca acaagcgccg actgtgg                                    27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 35
gggttgacca acaagcgccg actgtay                                    27

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 36
cccacaagct ccgactgtag gcgct                                      25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 37
cccacaagct ccgactgtag gcgcc                                      25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 38
aatggaagaa agtgaacttg atgctc                                     26

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 39
cattcctctt cgcatttcct gg                                         22

<210> SEQ ID NO 40
```

```
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 40
gcagaataca ttcaaggttt                                              20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 41
ggagcaaatg actggcgct                                               19

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 42
ggtttcaaag cgccagtcat ttgctcc                                      27

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Primer
<223> OTHER INFORMATION: This primer has a 5'-ribo-region

<400> SEQUENCE: 43
aatggaagaa agtgaacttg atgctc                                       26

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 44
ggtcgccgcg atcaaggagt                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 45
cggcacgctc acgtgacaga                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer
```

<400> SEQUENCE: 46
actccttgat cgcggcgacc                                                                              20

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 47
cgacagtcgg cgcttgtg                                                                                18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 48
cgacagtcgg cgcttgta                                                                                18

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 49
catggaccag aacaacccgc tgtcg                                                                        25

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 50
ccagaacaac ccgctgtc                                                                                18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 51
ccagaacaac ccgctgtt                                                                                18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 52
cgctgtcgag gttgaccc                                                                                18

<210> SEQ ID NO 53
<211> LENGTH: 18

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 53
cgctgtcgag gttgacct                                                     18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 54
gctgtcgagg ttgaccca                                                     18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 55
gctgtcgagg ttgaccct                                                     18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 56
ccataagcgc cgactgtc                                                     18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 57
ccataagcgc cgactgtg                                                     18

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 58
ctccagcccg gcacgctcac gt                                                22
```